(12) United States Patent
Wu et al.

(10) Patent No.: US 9,249,144 B2
(45) Date of Patent: Feb. 2, 2016

(54) PROCESS AND INTERMEDIATES FOR THE SYNTHESIS OF 8-[{1-(3,5-BIS-(TRIFLUOROMETHYL)PHENYL)-ETHOXY}-METHYL]-8-PHENYL-1,7-DIAZA-SPIRO[4.5] DECAN-2-ONE COMPOUNDS

(71) Applicant: OPKO Health, Inc., Miami, FL (US)

(72) Inventors: George G. Wu, Basking Ridge, NJ (US); Gerald Werne, Ketsch (DE); Xiaoyong Fu, Edison, NJ (US); Robert K. Orr, Cranford, NJ (US); Frank Xing Chen, Plainsboro, NJ (US); Jian Cui, Edison, NJ (US); Victoria M. Sprague, Bridgewater, NJ (US); Fucheng Zhang, Edison, NJ (US); Ji Xie, Edison, NJ (US); Liansheng Zeng, Union, NJ (US); Louis Peter Castellanos, Union City, NJ (US); Yuyin Chen, Garwood, NJ (US); Marc Poirier, Stewartsville, NJ (US); Ingrid Mergelsberg, Mahwah, NJ (US)

(73) Assignee: OPKO Health, Inc., Miami, FL (US)

( * ) Notice: Subject to any disclaimer, the term of this patent is extended or adjusted under 35 U.S.C. 154(b) by 0 days.

(21) Appl. No.: 14/043,210

(22) Filed: Oct. 1, 2013

(65) Prior Publication Data
US 2014/0031549 A1  Jan. 30, 2014

Related U.S. Application Data

(63) Continuation of application No. 13/062,454, filed as application No. PCT/US2009/056020 on Sep. 4, 2009, now abandoned.

(60) Provisional application No. 61/094,474, filed on Sep. 5, 2008.

(51) Int. Cl.
| | |
|---|---|
| *C07D 471/10* | (2006.01) |
| *C07D 207/267* | (2006.01) |
| *C07C 217/48* | (2006.01) |
| *C07D 498/04* | (2006.01) |
| *C07D 207/26* | (2006.01) |

(52) U.S. Cl.
CPC ............ *C07D 471/10* (2013.01); *C07C 217/48* (2013.01); *C07D 207/26* (2013.01); *C07D 207/267* (2013.01); *C07D 498/04* (2013.01)

(58) Field of Classification Search
CPC ............... C07D 207/06; C07D 471/10; C07D 207/267; C07C 217/48
USPC ........................................................ 546/16
See application file for complete search history.

(56) References Cited

U.S. PATENT DOCUMENTS

| | | |
|---|---|---|
| 5,620,989 A | 4/1997 | Harrison et al. |
| 5,760,018 A | 6/1998 | Baker et al. |
| 6,162,805 A | 12/2000 | Hefti |
| 6,215,019 B1 | 4/2001 | Pederson et al. |
| 6,635,768 B1 | 10/2003 | Hermann et al. |
| 7,049,320 B2 | 5/2006 | Paliwal et al. |
| 7,122,677 B2 | 10/2006 | Reichard et al. |
| 7,563,801 B2 | 7/2009 | Qiu et al. |
| 7,709,641 B2 | 5/2010 | Shah et al. |
| 7,902,366 B2 | 3/2011 | Paliwal et al. |
| 7,981,905 B2 | 7/2011 | Qiu et al. |
| 8,026,364 B2 | 9/2011 | Shah et al. |
| 8,178,550 B2 | 5/2012 | Hu et al. |
| 8,273,895 B2 | 9/2012 | Paliwal et al. |
| 8,361,500 B2 | 1/2013 | Qiu et al. |
| 8,404,702 B2 | 3/2013 | Qiu et al. |
| 8,470,842 B2 | 6/2013 | Hu et al. |
| 8,552,191 B2 | 10/2013 | Mergelsberg et al. |
| 8,754,216 B2 | 6/2014 | Shah et al. |
| 8,796,299 B2 | 8/2014 | Paliwal et al. |
| 2001/0029297 A1 | 10/2001 | Ashwood et al. |
| 2006/0007540 A1 | 1/2006 | Okuyama |
| 2008/0003640 A1 | 1/2008 | Hsu et al. |
| 2011/0038925 A1 | 2/2011 | Wan et al. |
| 2013/0122088 A1 | 5/2013 | Qiu et al. |
| 2013/0281477 A1 | 10/2013 | Hu et al. |
| 2014/0024834 A1 | 1/2014 | Mergelsberg et al. |
| 2014/0088128 A1 | 3/2014 | Qiu et al. |
| 2014/0296196 A1 | 10/2014 | Palani et al. |
| 2014/0336158 A1 | 11/2014 | Paliwal et al. |

FOREIGN PATENT DOCUMENTS

| | | |
|---|---|---|
| EP | 0850902 A1 | 7/1998 |
| EP | 1905777 A1 | 4/2008 |
| WO | WO-94/10165 A1 | 5/1994 |
| WO | WO-94/13639 A1 | 6/1994 |

(Continued)

OTHER PUBLICATIONS

U.S. Appl. No. 13/062,454, filed Mar. 4, 2011, Wu et al.

(Continued)

*Primary Examiner* — Rita Desai

(74) *Attorney, Agent, or Firm* — Choate, Hall & Stewart LLP; Brenda Herschbach Jarrell; Kristen C. Buteau

(57) ABSTRACT

This application discloses a novel process to synthesize 8-[{1-(3,5-Bis-(trifluoromethyl)phenyl)-ethoxy}-methyl]-8-phenyl-1,7-diaza-spiro[4.5]decan-2-one compounds, which may be used, for example, as NK-1 inhibitor compounds in pharmaceutical preparations, intermediates useful in said process, and processes for preparing said intermediates; also disclosed is a process for removal of metals from N-heterocyclic carbine metal complexes.

7 Claims, No Drawings

(56) References Cited

FOREIGN PATENT DOCUMENTS

| WO | WO-95/19344 A1 | 7/1995 |
|---|---|---|
| WO | WO-99/51344 A1 | 10/1999 |
| WO | WO-00/71554 A2 | 11/2000 |
| WO | WO-01/44200 A2 | 6/2001 |
| WO | WO-02/14376 A2 | 2/2002 |
| WO | WO-03/051840 A1 | 6/2003 |
| WO | WO-2004/035596 A1 | 4/2004 |
| WO | WO-2005/100358 A1 | 10/2005 |
| WO | WO-2006/007540 A1 | 1/2006 |
| WO | WO-2007/003135 A1 | 1/2007 |
| WO | WO-2007/114921 A2 | 10/2007 |
| WO | WO-2007/114922 A2 | 10/2007 |
| WO | WO-2007/117486 A2 | 10/2007 |
| WO | WO-2008/118328 A2 | 10/2008 |
| WO | WO-2008/118331 A2 | 10/2008 |
| WO | WO-2010/028232 A1 | 3/2010 |
| WO | WO-2011/019911 A1 | 2/2011 |

OTHER PUBLICATIONS

U.S. Appl. No. 14/540,635, filed Nov. 13, 2014, Qiu et al.
U.S. Appl. No. 14/683,871, filed Apr. 10, 2015, Hu et al.
Cogan et al., Asymmetric Synthesis of Chiral Amines by Highly Diastereoselective 1,2-Additions of Organometallic Reagents to N-tert-Butanesulfinyl Imines, Tetrahedron, 55: 8883-8904 (1999).
Duffy et al., Potential therapeutic targets for neurokinin-1 receptor antagonists, Expert Opinion on Emerging Drugs, 9(1): 9-21 (2004).
Giard et al., Pyrrolidines bearing a quaternary α-stereogenic center. Part 1: Synthesis of analogs of ABT-418, a powerful nicotinic agonist, Tetrahedron Letters, 40: 5495-5497 (1999).
Gonzales et al., Antiemetic Agents in Cancer Chemotherapy, Oncology Special Edition, 5:53-58 (2002).
Harrison, T. et al., Gem-disubstituted amino-ether based substance P antagonists, Bioorganic & Medicinal Chemistry Letters, 4(23): 2733-2734 (1994).
International Search Report of PCT/US09/56020, 5 pages (Jan. 4, 2010).
Kramer et al., Distinct Mechanism for Antidepressant Activity by Blockade of Central Substance P Receptors, Science, 281: 1640-1645 (1998).
Kubik et al., Synthesis of α,α-Dialkylated Amino Acides with Adenine of Thymine Residues A New Mild and Facile Hydrolysis for Hydantoins, Tetrahedron Letters, 35(36): 6635-6638 (1994).
O'Donnell et al., New Methodology for the Synthesis of α,α-Dialkylamino Acids Using the Self-Regeneration of Stereocenters Method: α:Ethyl-α-Phenylglycine, Heterocycles, 46: 617-630 (1997).
Rogiers et al., Stereoselective conversion of 2H-1,4-oxazin-2-ones into 2,5,5-substituted piperidine-2-carboxamides and 2-methanamines and related octahydro-2H-pyrido[1,2-a]pyrazines, potential substance P antagonists, Tetrahedron, 57: 8971-8981 (2001).
Rombouts et al., Intramolecular Diels-Alder reactions of N-alkenyl-2(1H)-pyrazinones: generation of a novel type of cis-1,7-naphthyridine, Tetrahedron Letters, 42: 7397-7399 (2001).
Wallace, Exploiting Catalyst Characteristics: A Protocol for Increasing Diastereoselectivity in a Double Ring-Closing Metathesis Reaction, Journal of Molecular Catalysis A: Chemical, 254(1-2): 78-84 (2006).
Written Opinion of PCT/US09/56020, 5 pages (Jan. 4, 2010).
Wu et al., Stereoselective Transformation of 2H-1,4-Oxazin-2-ones into 2,(2),5,5-Tri- and Tetrasubstituted Analogues of cis-5-Hydroxy-2-piperidinemethanol and cis-5-Hydroxy-6-oxo-2-piperidinecarboxylic Acid, Tetrahedron, 56: 3043-3051 (2000).

PROCESS AND INTERMEDIATES FOR THE SYNTHESIS OF 8-[{1-(3,5-BIS-(TRIFLUOROMETHYL)PHENYL)-ETHOXY}-METHYL]-8-PHENYL-1,7-DIAZA-SPIRO[4.5]DECAN-2-ONE COMPOUNDS

CROSS-REFERENCE TO RELATED APPLICATIONS

This application of U.S. application No. 13/062,454, filed Mar. 4, 2011, now abandoned, which is a national phase application under 35 U.S.C. §371 of International application No. PCT/US09/56020, filed Sep. 4, 2009, which claims priority to U.S. Provisional Application No. 61/094,474, filed Sep. 5, 2008, the entirety of each of which is hereby incorporated by reference.

FIELD OF THE INVENTION

This application pertains to processes useful in the preparation of 8-[{1-(3,5-Bis-(trifluoromethyl)phenyl)-ethoxy}-methyl]-8-phenyl-1,7-diaza-spiro[4.5]decan-2-one compounds and intermediates useful in the synthesis thereof, and the intermediate compounds prepared thereby.

BACKGROUND OF THE INVENTION

Identification of any publication, patent, or patent application in this section or any section of this application is not an admission that such publication is prior art to the present invention.

The preparation of diazaspirodecan-2-ones for example, 8-[{1-(3,5-Bis-(trifluoromethyl)phenyl)-ethoxy}-methyl]-8-phenyl-1,7-diaza-spiro[4.5]decan-2-one, for example, (5S, 8S)-8-[{(1R)-1-(3,5-Bis-(trifluoromethyl)phenyl)-ethoxy}-methyl]-8-phenyl-1,7-diazaspiro[4.5]decan-2-one (the compound of Formula I) has been described in U.S. Pat. No. 7,049,320 (the '320 patent), issued May 23, 2006, the disclosure of which is incorporated herein in its entirety by reference.

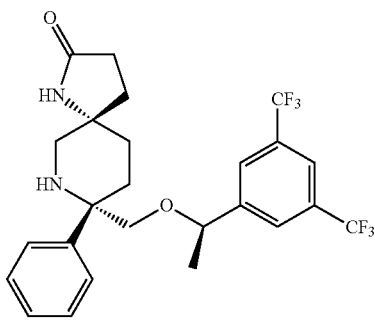

Formula I

The compounds described in the '320 patent are classified as tachykinin compounds, and are antagonists of neuropeptide neurokinin-1 receptors (herein, "NK-1" receptor antagonists). Other $NK_1$ receptor antagonists and their synthesis have been described, for example, those described in Wu et al, *Tetrahedron* 56, 3043-3051 (2000); Rombouts et al, *Tetrahedron Letters* 42, 7397-7399 (2001); and Rogiers et al, *Tetrahedron* 57, 8971-8981 (2001) and in published International Application No. WO05/100358, each of which is incorporated herein in their entirety by reference. A process for preparing the compound of Formula I is also disclosed in U.S. Application No. 2008/003640, filed Mar. 20, 2008 (the '640 application).

"NK-1" receptor antagonists have been shown to be useful therapeutic agents, for example, in the treatment of pain, inflammation, migraine, emesis (vomiting), and nociception. Among many compounds disclosed in the above-mentioned '320 patent are several novel diazaspirodecan-2-ones, including the compound of Formula I, which are useful in the treatment of nausea and emesis associated with any source of emesis, for example, emesis associated with recovery from anesthesia or chemotherapy treatments (Chemotherapy-induced nausea and emesis, herein, CINE).

The synthesis method for preparing the compound of Formula I described in the '320 patent generally follows Scheme A in the provision of 8-[{1-(3,5-Bis-(trifluoromethyl)phenyl)-ethoxy}-methyl]-8-phenyl-1,7-diaza-spiro[4.5]decan-2-one compounds.

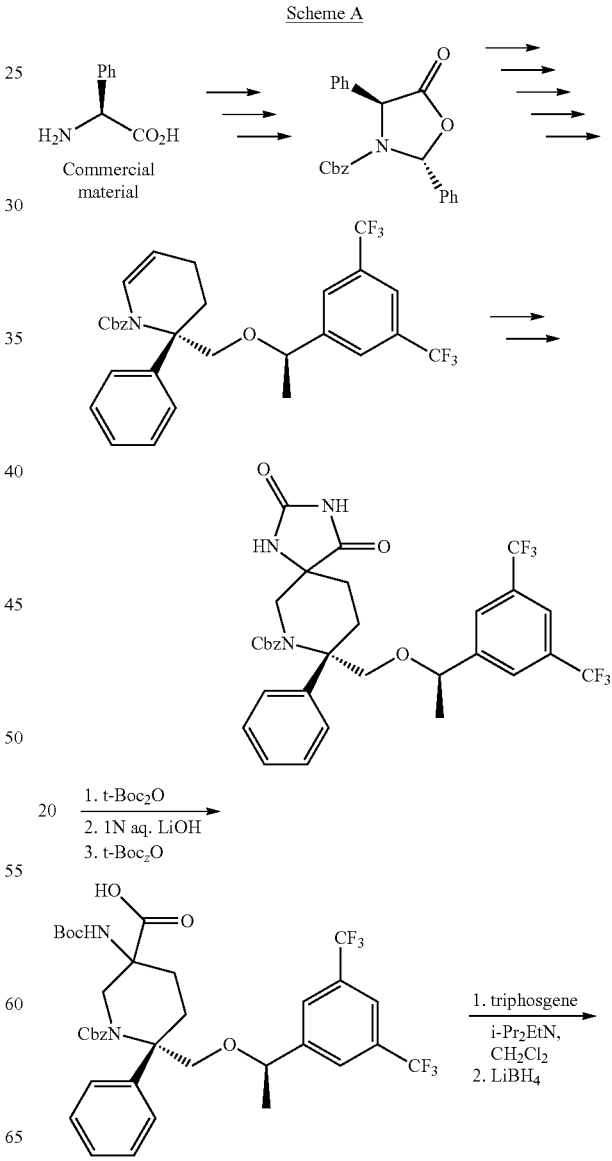

Scheme A

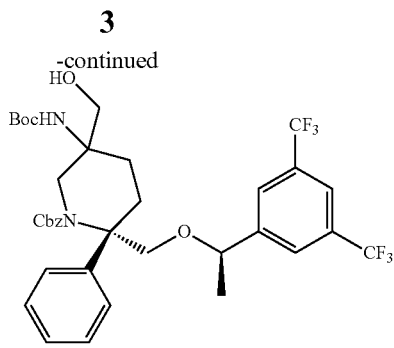

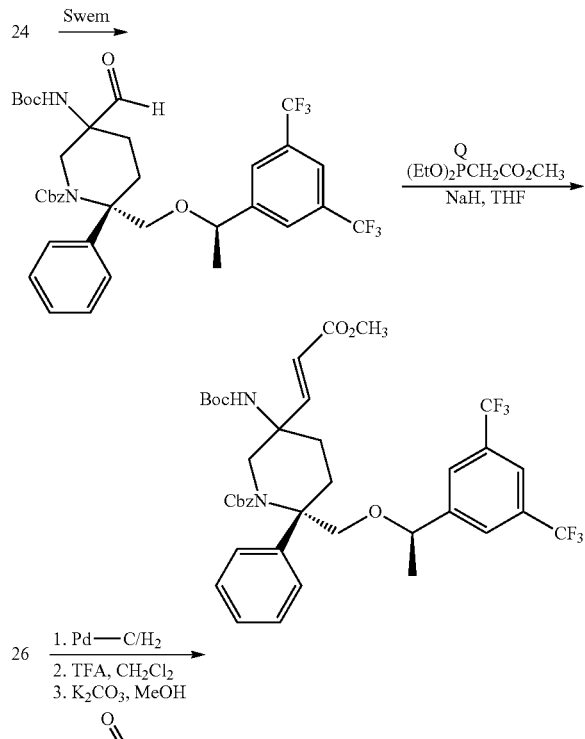

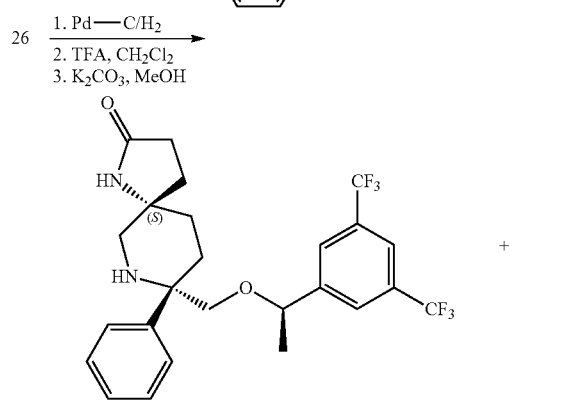

The process for the preparation of the compound of Formula I described in the '320 patent is carried out in 18 individual steps from commercially available starting materials, and in many steps of the process described in the '320 patent, intermediate compounds must be isolated or isolated and purified before use in a subsequent step, often utilizing column chromatography for that purpose. In general, the synthetic scheme described in the '320 patent consumes a larger than desirable percentage of starting and intermediate compounds in the production of unwanted isomers.

The process for the preparation of the compound of Formula I described in the '640 application generally follows Scheme B:

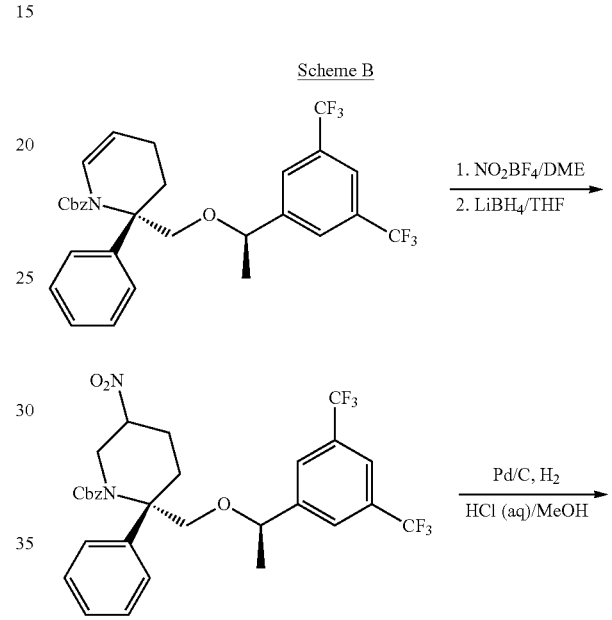

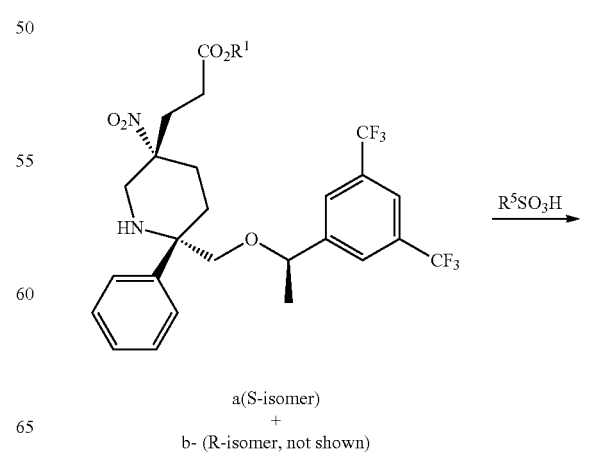

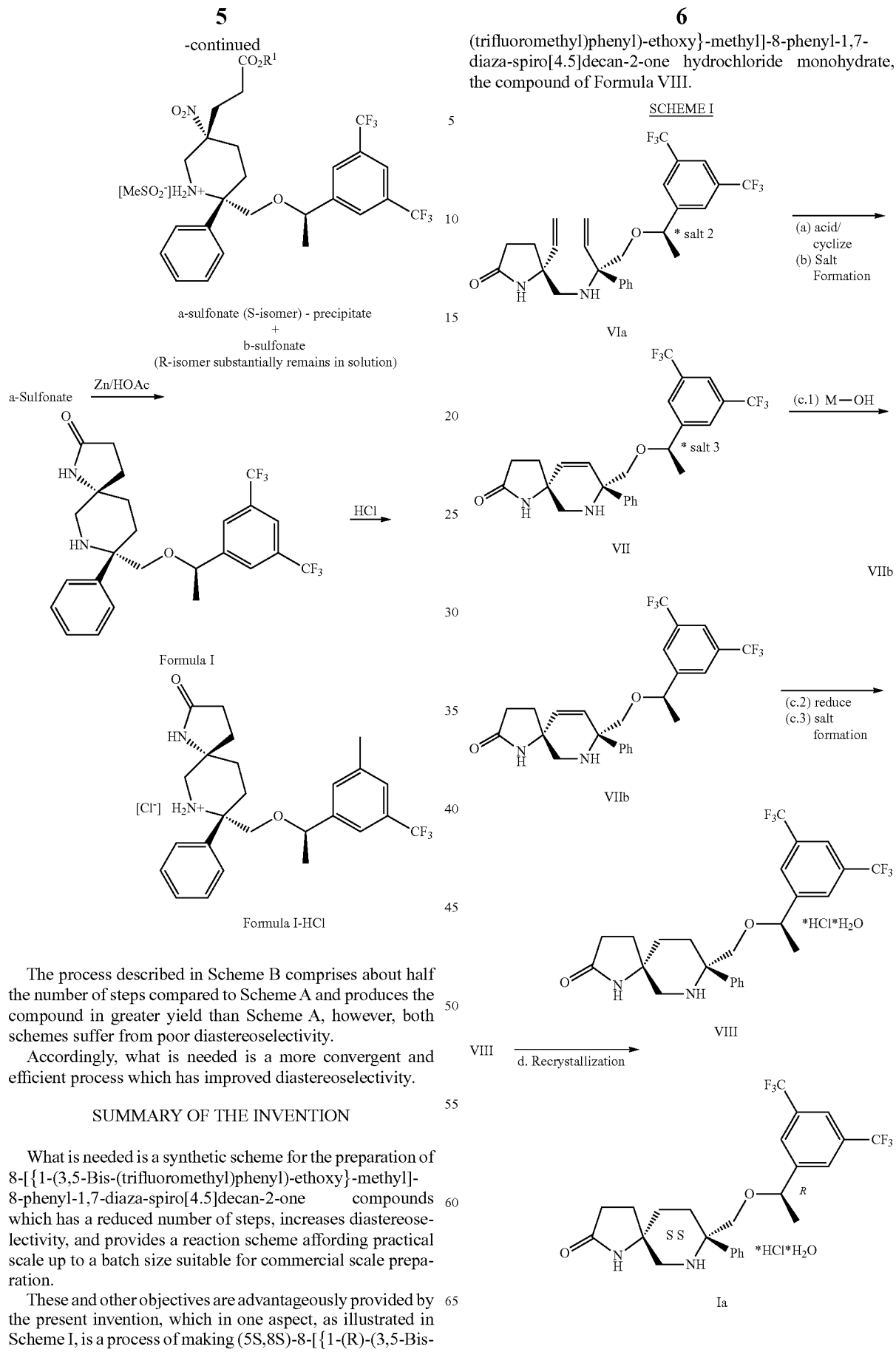

The process described in Scheme B comprises about half the number of steps compared to Scheme A and produces the compound in greater yield than Scheme A, however, both schemes suffer from poor diastereoselectivity.

Accordingly, what is needed is a more convergent and efficient process which has improved diastereoselectivity.

SUMMARY OF THE INVENTION

What is needed is a synthetic scheme for the preparation of 8-[{1-(3,5-Bis-(trifluoromethyl)phenyl)-ethoxy}-methyl]-8-phenyl-1,7-diaza-spiro[4.5]decan-2-one compounds which has a reduced number of steps, increases diastereoselectivity, and provides a reaction scheme affording practical scale up to a batch size suitable for commercial scale preparation.

These and other objectives are advantageously provided by the present invention, which in one aspect, as illustrated in Scheme I, is a process of making (5S,8S)-8-[{1-(R)-(3,5-Bis-(trifluoromethyl)phenyl)-ethoxy}-methyl]-8-phenyl-1,7-diaza-spiro[4.5]decan-2-one hydrochloride monohydrate, the compound of Formula VIII.

wherein the process comprises:

a) providing the salt compound of Formula VIa, [5(R)-[[[1(S)-[[1(R)-[3,5-bis(trifluoromethyl)-phenyl]ethoxy]-methyl]-1-phenyl-2-propenyl]amino]methyl]-5-ethenyl-2-pyrrolidinone] [Salt 2], wherein "Salt 2" represents at least one proton bonded to a base functional group in the compound of Formula VIa, for example, a nitrogen electron pair, thus forming an ammonium cation, and associated therewith a coordinated anion moiety, for example, the conjugate base of an acid, and cyclizing the diene-amine salt compound of Formula VIa using a ring closing metathesis catalyst;

b) converting the cyclized product from Step (a) to a salt to obtain the compound of Formula VII [(5R,8S)-8-[1-(R)-(3,5-bis-trifluoromethyl-phenyl)-ethoxymethyl]-8-phenyl-1,7-diazaspiro[4.5]dec-9-en-2-one] Salt 3, wherein "Salt 3" represents at least one proton bonded to a base functional group in the compound of Formula VII and associated therewith a coordinated anion moiety;

c) treating from the salt compound of Formula VII provided in Step (b) with a hydroxide base of Formula M-OH, for example, wherein "M" is a alkaline metal or alkali earth metal, to provide the corresponding freebase compound of Formula VIIb, reducing the freebase compound of Formula VIIb and treating the reduction product with HCl to obtain the 1,7-diazaspiro[4.5]dec-2-one hydrochloride hydrate of Formula VIII; and d) optionally recrystallizing the HCl salt of Formula VIII thereby obtaining the compound of Formula Ia.

In some embodiments of Scheme I, it is preferred to carry out the reduction in Step "c" on the salt compound of Formula VII without liberating the freebase form thereform and recovering the reduced salt product produced thereby instead of precipitating the salt of the freebase reduction product.

In some embodiments of the present invention, preferably Step (a) of Scheme I is carried out in the presence of a sufficient amount of added acid to decrease the loading (amount of catalyst present) of the ring-closing metathesis catalyst employed. In some embodiments of Scheme I using added acid in Step (a), it is preferred to use an acid having a pKa which is about equal to or less than that of the diene compound of Formula VI being cyclized in the reaction, for example, an acid having a pKa equal to or less than 6.5. In some embodiments of Scheme I employing added acid in Step (a), it is preferred for the acid to be: (i) a mineral acid, for example, HCl, HBr, or sulfuric acid; (ii) a mono- or di-organic acid, for example, acetic, proponoic, maleic, fumaric, trifluoroacetic, or tartatic acids; or (iii) a sulfonic acid, for example, an alkyl-sulfonic acid or substituted alkylsulfonic acid, for example, methanesulfonic acid, 4-methylbenzenesulfonic acid monohydrate, or trifluoromethanesulfonic acid, or an aromatic arylsulfonic acid, for example p-toluenesulfonic acid or a substituted arylsulfonic acid. In some embodiments utilizing an excess acid in Step 2, the acid is preferably an arylsulfonic acid, more preferably p-tolysulfonic acid. In some embodiments employing excess acid in Step 2, it is preferred to add the acid in an amount of from about 0.1 to about 2.0 equivalents relative to the amount of substrate initially present in the reaction mixture.

In some embodiments of Scheme I it is preferred to carry out the cyclization reaction in Step (a) by the process illustrated in Scheme Ia.

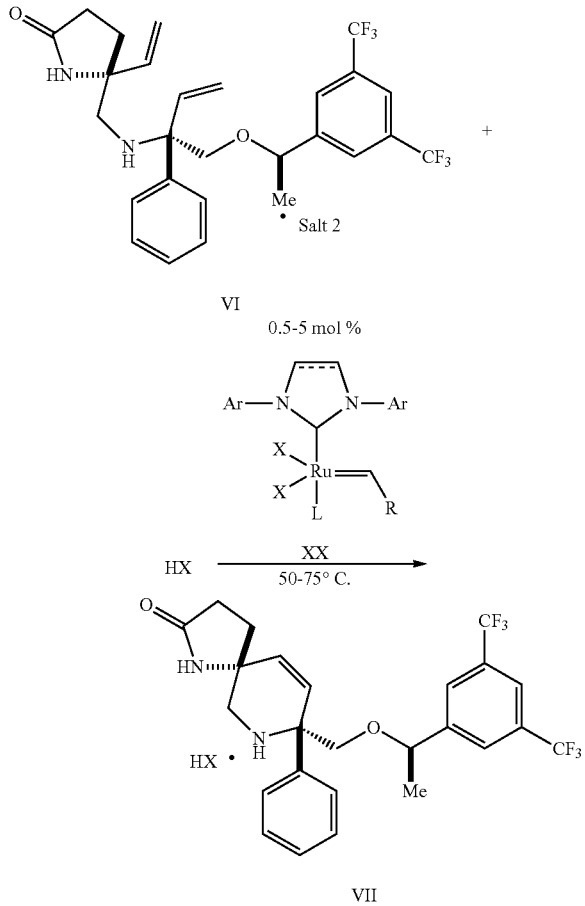

SCHEME Ia wherein
the dotted line of the compound of Structure XX represents an optional double bond and "Salt 2" is as defined above;

Ar is an aryl moiety, for example, phenyl or mesityl (2,4,6-trimethylphenyl);

L is $P(R^{2a})_3$, wherein $R^{2a}$ is selected independently and is phenyl, aryl, alkoxylphenyl or alkyl;

M is a metal which is ruthenium, palladium, or iridium;

X is halogen;

R is H, aryl, or heteroaryl; and

HX is an acidic species, preferably where "X" is: halogen, for example, chloride, bromide, or iodide; sulfate; sulfite; or a sulfonate moiety, for example, mesylate, trifluoromethylsulfonate, or an aryl sulfonate, for example tosylate, the process comprising:

(i) contacting a secondary amine salt of Formula VI with an acid of the Formula HX;

(ii) adding a ring closing metathesis catalyst to the mixture from step (i), preferably in an amount which is sub-stoichiometric with respect to the amount of the compound of Formula VI used; and (iii) heating the mixture to cyclize the compound of Formula VI.

In some embodiments of Scheme 1a, the ring-closing metathesis catalyst used in the reaction is preferably selected from the compounds of Formulae XXa, XXb, or XXd:

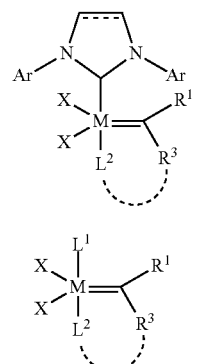

XXa

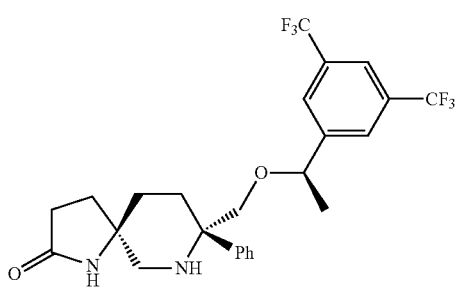

Ic

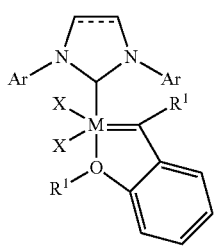

XXb

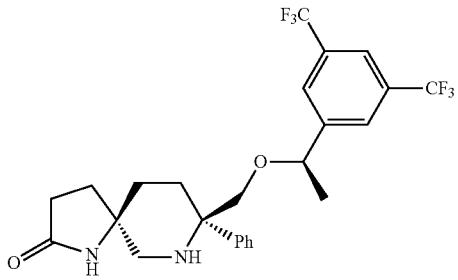

Id

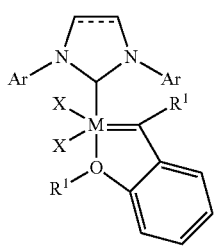

XXd

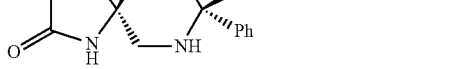

where the metal (M) is preferably a transition metal with a formal oxidation state providing 8 "d" orbital electrons (a group 8 transition metal, for example, ruthenium, palladium or iridium, or a group 6 transition metal, for example, molybdenum), "$L^1$" is a sigma-bonded carbon ligand with substantial Pi-backbonding capability, for example, the imidazole ligand shown in the compounds of Formulae XXa and XXd, and $L^2$ is a monodentate ligand, for example, a phosphine ligand, for example ($Cy_3P$), or, as indicated, $L^2$ is optionally bonded to the $R^3$ substituent of the carbene (ligand, and when optionally bonded to the carbene ligand via $R^3$, illustrated by the semicircular dotted line between $L^2$ and $R^3$, $L^2$ forms a bidentate ligand, and $L^2$ is a chelating moiety, for example, an oxygen, phosphorous, or nitrogen moiety, for example, the oxygen moiety in the alkoxybenzylidene bidentate ligand shown in the catalyst of Formula XXd, for example, an isoproxy-benzylidene ligand, $R^1$ is independently selected from aryl, heteroaryl, alkyl, or hydrogen, $R^3$ is an alkyl heteroaryl or aryl, for example, a phenyl moiety, or when $R^3$ is not bonded to $L^2$, $R^3$ may be hydrogen, and (X) is a conjugate base of a strong acid, preferably X is a sulfonate moiety, for example, tosylate, or halogen moiety, for example, chloride.

It will be appreciated that in reaction Scheme I shown above, although the compound of Formula Ia is the (S,S,R) enantiomer, the process of the invention can be employed using starting materials of the appropriate stereoisomer configuration to prepare all of the isomers of the compound of Formula I, i.e.,

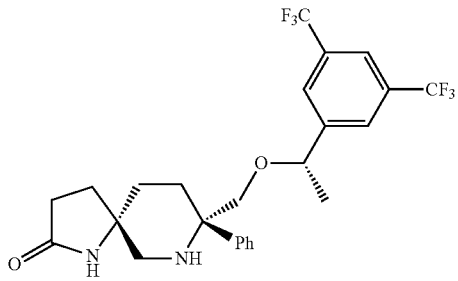

Ie

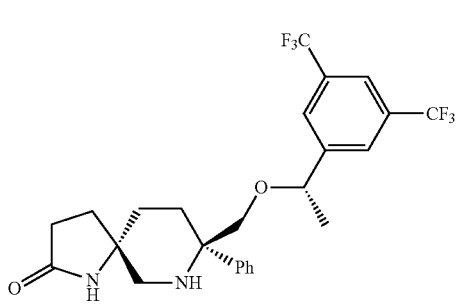

If

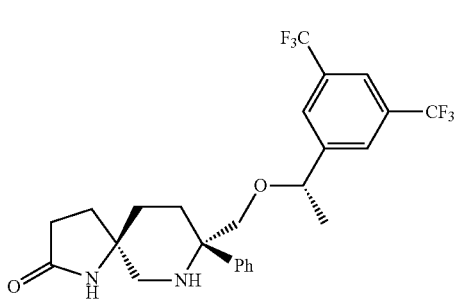

Ig

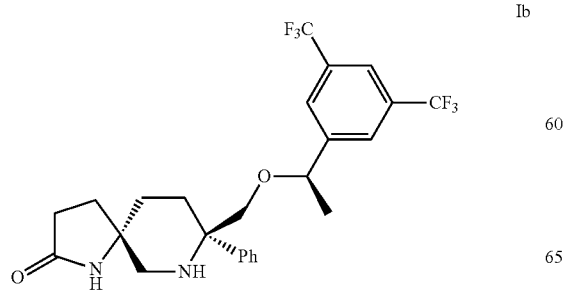

Ib

-continued

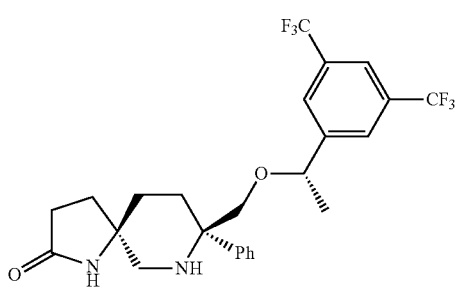

Ih

In some embodiments of the invention it is preferred to provide the compound of Formula VIa used in Scheme I by the process of Scheme Iaa SCHEME Iaa

II

↓ Base

III

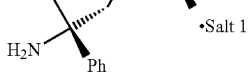

V

1. Reduction
2. Salt Formation
→ VIa wherein the process comprises:
a) providing the pyrazolo-5-one of Formula III;
b) providing the freebase compound of Formula IV, [(1S)-1-({(1R)-1-[3,5-bis(trifluoromethyl)phenyl]ethoxy}methyl)-1-phenylprop-2-enyl)amine, and reacting it with the compound of Formula III provided in Step (a) to yield the diene-imine of Formula V, [((5R)-5-((Z)-{[(1S)-1-({(1R)-1-[3,5bis(trifluoromethyl)-phenyl]-ethoxy}methyl)-1-phenylprop-2-en-1-yl]imino}methyl)-5-vinylpyrrolidin-2-one)];
c) reducing the diene-imine compound of Formula V prepared in Step (b) to obtain the corresponding diene-amine compound, converting it to the corresponding salt compound of Formula VI, [5(R)-[[[1(S)-[[1(R)-[3,5-bis(trifluoromethyl)-phenyl]ethoxy]-methyl]-1-phenyl-2-propenyl]amino]methyl]-5-ethenyl-2-pyrrolidinone] [Salt 2], wherein "Salt 2" represents at least one proton bonded to a base functional group in the compound of Formula VI, for example, the electron pair in a nitrogen atom in the compound, and associated therewith a coordinated anion moiety.

In some embodiments of the present invention it is preferred to provide the pyrazolo-5-one compound of Formula III in Step (a) of Scheme 1aa by treating the compound of Formula II, (3R)-(1,1-dimethylethyl)-7aR-ethenyltetrahydro-1 (R/S)-hydroxy-3H,5H-pyrrolo[1,2-c]oxazol-5-one, with an appropriate base, for example, triethylamine. In some embodiments of the present invention it is preferred to provide the free-base compound of Formula IV in Step (b) of Scheme 1aa by treating the corresponding salt compound of Formula IVa with a water soluble base, for example, sodium hydroxide, Formula IVa

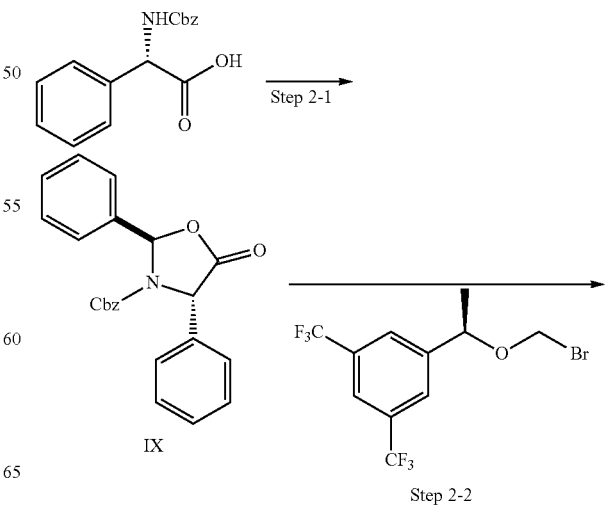

wherein Salt 1 represents at least one proton bonded to a base functional group, for example, the amine substituent, in the compound of Formula IVa and associated therewith a coordinated anion moiety. Suitable acids for preparing the salt compounds of Formula IVa are, for example: organic acids, for example, maleic acid, succinic acid, or malic acid; and inorganic acids, for example, HCl, HBr, and HI.

In some embodiments of the present invention, in Step 2, preferably, the ring-closing metathesis catalyst is a ring-closing metathesis catalyst of Formula XX, described in Scheme 4 (below).

In some embodiments of the present invention it is preferred to prepare the intermediate of Formula IV using the process illustrated in Scheme 2, steps 2-3 and beyond. In some embodiments it is preferred to provide the intermediate of Structure X for use in preparing the compound of Formula IV as shown in Scheme II, steps 2-1 and 2-2.

Scheme 2

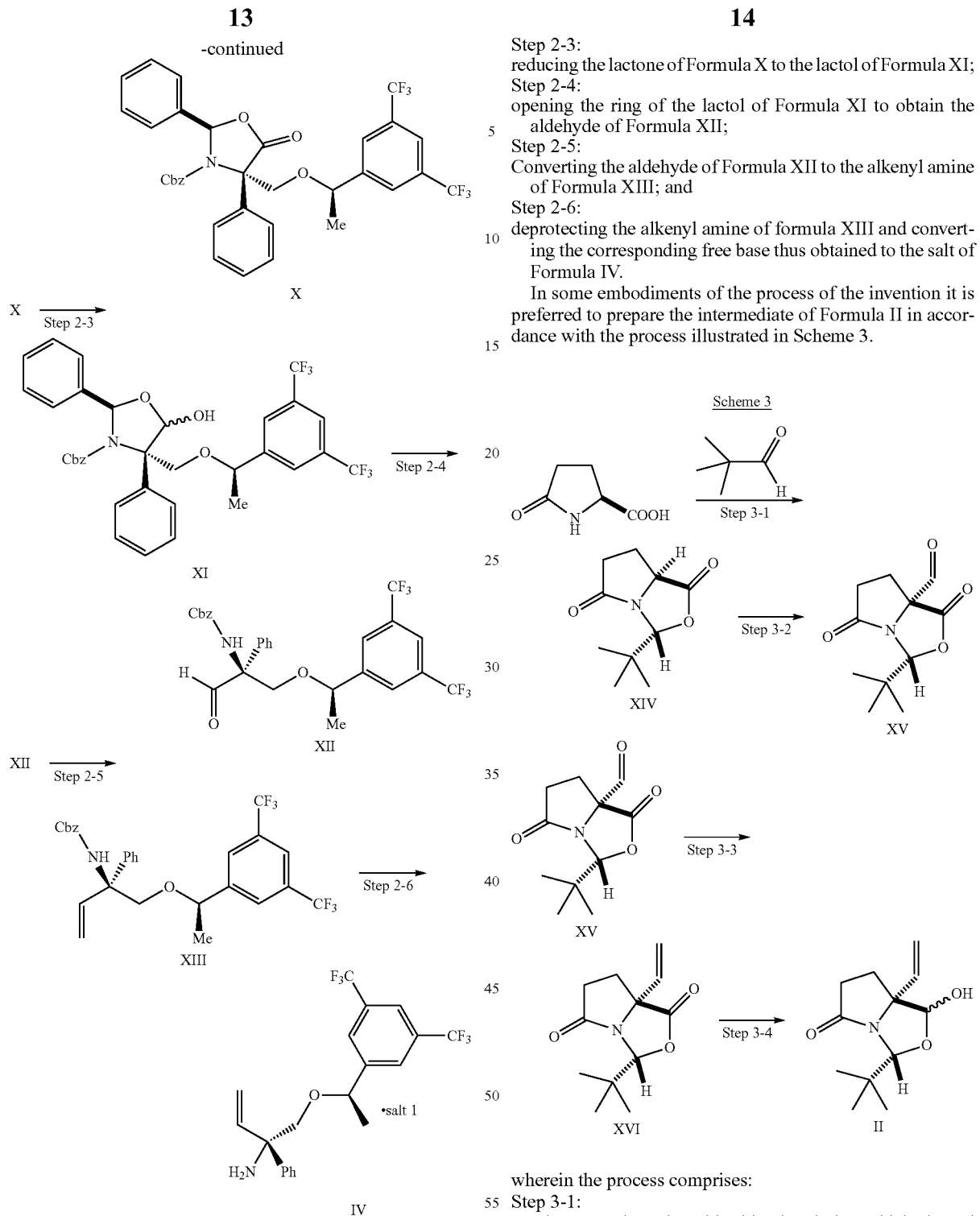

Step 2-3:
reducing the lactone of Formula X to the lactol of Formula XI;
Step 2-4:
opening the ring of the lactol of Formula XI to obtain the aldehyde of Formula XII;
Step 2-5:
Converting the aldehyde of Formula XII to the alkenyl amine of Formula XIII; and
Step 2-6:
deprotecting the alkenyl amine of formula XIII and converting the corresponding free base thus obtained to the salt of Formula IV.

In some embodiments of the process of the invention it is preferred to prepare the intermediate of Formula II in accordance with the process illustrated in Scheme 3.

wherein the process comprises:
Step 3-1:
treating pyroglutamic acid with trimethylacetaldehyde and methanesulfionic acid to obtain (3R,6S)-3-tert-butyldihydro-1H-pyrrolo[1,2-c][1,3]oxazole-1,5(6H)-dione of Formula XIV;
Step 3-2:
reacting the pyrrolo[1,2-c][1,3]oxazole-1,5(6H)-dione of Formula XIV with methyl formate to obtain the pyrrolo[1,2-c]oxazole-7a-carbaldehyde of Formula XV;
Step 3-3:
converting the carbaldehyde of Formula XV to the 7a-vinyl-dihydro-pyrrolo[1,2-c][1,3]oxazole-1,5-dione of Formula XVI; and wherein the process comprises:
Step 2-1:
cyclyzing the 2-phenylglycine derivative shown with PhCH(OCH₃)₂ to obtain the oxazolidinone of Formula IX, wherein Cbz is a carboxybenzyl-amine protecting group;
Step 2-2:
combining the compound of Formula IX with [3,5-bis(trifluoromethyl)phenyl]-ethoxy-bromomethyl ether to obtain the lactone of Formula X;

Step 3-4:

reducing the dione of Formula XVI to obtain the (3R)-1,1-dimethyl-7a(R)-ethenyl-tetrahydro-1(R/S)-hydroxy-3H,5H=pyrrolo[1,2-c]oxazol-5-one of Formula II.

Another aspect of the present invention relates to the following novel intermediates used or prepared in the processes represented in Schemes 1-3:

II

III

IVa

V

VI or a salt thereof or a salt thereof

Scheme 4 illustrates a chemical process for removing metathesis catalyst from the reaction mixture after ring closure is complete. In some embodiments of the present invention it is preferred to employ the chemical process illustrated in Scheme 4 at the end of reaction Step 2 shown in Scheme 1 to removal of the metal associated with the metathesis catalyst employed in the cyclization reaction. Accordingly, Scheme 4 illustrates removal of a metathesis catalyst of Formula XXa', preferably the complex of Formula XXa' is an N-heterocyclic carbine metal complex, but it will be appreciated that the process can be employed to chemically remove any metal metathesis catalyst from the reaction mixture.

Scheme 4

XXa'

$$ML_2 \ + \ [\ldots]$$

wherein
the dotted lines represent optional bonds;
Ar is phenyl, 2,4,6-trimethylphenyl, or 2,6-dimethylphenyl;
M is preferably a transition metal with a formal oxidation state providing 8 "d" orbital electrons (a group 8 transition metal, for example, ruthenium, palladium or iridium) or a group 6 transition metal, for example, molybedinum;
$L^2$ is a phosphine ligand, for example, $P(R)_3$, where "R" is phenyl aryl, or alkyl, for example, $(Cy)_3P$, or optionally, $L^2$ is bonded to the carbene substituent via $R^3$, indicated by the semicircular dotted line between $L^2$ and $R^3$, forming a bidentate ligand, wherein $L^2$ is a chelating moiety, for example, an oxygen, phosphorous, or nitrogen moiety, for example, the oxygen moiety in the isoproxybenzylidene bidentate ligand shown in the catalyst of Formula XXd (herein), R¹ is independently selected from aryl, alkyl, or hydrogen; R² is H, OH, or =O;

R³ is an aryl, alkyl or phenyl moiety, or H if L² is not bonded to R³, and (X) is a conjugate base of a strong acid, for example, a halogen, a sulfate, sulfite or sulfonate anion, preferably "X" is a sulfonate anion, for example tosylate or a halogen moiety which is chloride or bromide, the process comprising:

(i) heating a mixture of an aqueous solution of a reducing reagent, preferably a reducing reagent which is sodium metabisulfite (Na₂S₂O₅), sodium sulfite (Na₂SO₃), sodium bisulfite (NaSO₃H), hypophosphorous acid (phosphinic acid, H₃PO₂), sodium formate (NaOCHO) or phosphorous acid sodium salt (NaH₂PO₃), or mixtures of two or more, in the presence of a solution comprising a water-immiscible organic solvent and at least one N-heterocyclic carbine metal complex of Formula [XX], [XXa], [XXb] or [XXd]; and (ii) separating the metal complex of Formula ML₂ from the organic layer after heating Step (i) by: (a) filtration where the metal complex is insoluble; or (b) where the metal complex is soluble, uptake of the metal complex into the aqueous layer and separating the organic and aqueous layers.

In some embodiments it is preferred to carry out the process of Scheme 4 in the presence of a phase transfer catalyst, for example a quaternary ammonium salt, for example, a quaternary ammonium salt of the Formula [(R^{a3})₄N]⁺X⁻, wherein R^{a3} is alkyl, for example, n-butyl-, and X is a halide, sulfonate, or nitrate.

In some embodiments it is preferred to employ as the reducing reagent: (i) one or more inorganic salt compounds, for example, Na₂S₂O₅, Na₂SO₃, or NaH₂PO₃; (ii) a phosphorous acid, for example, H₃PO₂; (iii) one or more metal hydride compounds, for example, sodium hydride, sodium borohydride, or lithium aluminum hydride; (iv) a reduction carried out with hydrogen and a catalyst, for example, palladium on carbon; (v) an organic reducing reagent, for example, ascorbic and oxalic acids; (vi) hydrogen peroxide; or (vii) one or more metal reducing reagents, for example, copper, zinc, iron or magnesium. It will be appreciated that while Scheme 4 is illustrated with the metathesis catalyst of Formula XXa, the process will yield similar results and advantages if used in the presence of any metathesis catalyst.

Other aspects and advantages of the invention will become apparent from following Detailed Description.

DETAILED DESCRIPTION OF THE INVENTION

Earlier processes for the preparation of the compound of Formula I include preparation of the piperidinyl moiety, followed by reactions to add the spiro pyrrolidinyl ring, while the presently claimed process cyclizes a 3,5-bis(trifluoromethyl)phenyl]ethoxy]methyl]-1-phenyl-2-propenyl]amino]methyl]-5-ethenyl-2-pyrrolidinone. Compared to previous procedures, the present invention for preparing the compound of Formula I is convergent and shorter, provides for improved enantiomeric and diastereomeric selectivity, provides the compound in higher yield, and is easier and more cost-effective to use.

Terms used in the general schemes herein, in the examples, and throughout the specification, include the following abbreviations, together with their meaning, unless defined otherwise at the point of their use hereinafter: Me (methyl); Bu (butyl); t-Bu (tertiary butyl); Cbz- (Carboxybenzyl); Et (ethyl); Ac (acetyl); t-Boc or t-BOC (t-butoxycarbonyl); DMF (dimethylformamide); THF (tetrahydrofuran); DIPEA (diisopropylethylamine); RT (room temperature, generally 25° C.); TFA (trifluoroacetic acid); TEA (triethyl amine); NMP (1-methyl-2-pyrrolidinone); MTBE or TBME (tert-butyl methyl ether); Me (methyl); Mes, when used as a structural substituent (mesityl, which is 2,4,6-trimethylphenyl-moiety); Ph (phenyl); NaHMDS (sodium hexamethyldisilizane); DMI (1,3-dimethyl-2-imidazolidinone); AcOH (acetic acid);

LHMDS (lithium bis(trimethylsilyl)amide);

TMSCl (chlorotrimethylsilane or trimethylsilyl chloride); TFAA (trifluoroacetic anhydride); and IPA (isopropanol).

As used herein, the following terms, unless otherwise indicated, are understood to have the following meanings:

Alkyl means a straight or branched chain aliphatic hydrocarbon having 1 to 6 carbon atoms.

Halogen means a halogen moiety, for example, fluoro, chloro, bromo or iodo.

PTC, a phase-transfer catalyst, an agent which facilitates transfer of a reactive moiety or reaction product from one phase to another phase in a reaction mixture.

A wavy line ∿∿ appearing on a structure and joining a functional group to the structure in the position of a bond generally indicates a mixture of, or either of, the possible isomers, e.g., containing (R)- and (S)-stereochemistry. For example,

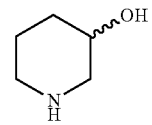

means containing either, or both of

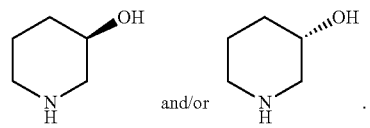 [SMILES: O[C@@H]1CCCNC1 ; O[C@H]1CCCNC1]

As well known in the art, a bond drawn from a particular atom wherein no moiety is depicted at the terminal end of the bond indicates a methyl group bound through that bond to the atom, unless stated otherwise. For example:

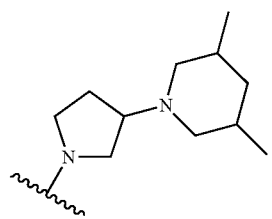

represents

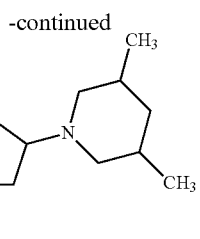

However, sometimes in the examples herein, the CH₃ moiety is explicitly included in a structure. As used herein, the use of either convention for depicting methyl groups is meant to be equivalent and the conventions are used herein interchangeably for convenience without intending to alter the meaning conventionally understood for either depiction thereby.

The term "isolated" or "in isolated form" for a compound refers to the physical state of said compound after being isolated from a process. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

In the reaction schemes depicting the present inventions, brackets around a structure indicate that the compound is not necessarily purified or isolated at that stage, but is preferably used directly in the next step. Also, various steps in the general reaction schemes do not specify separation or purification procedures for isolating the desired products, but those skilled in the art will recognize that well known procedures are used.

Typical parameters for the process described in Scheme 1 are discussed below.

With reference to Scheme I, above, in some embodiments step 1 is typical carried out in accordance with the following reaction scheme:

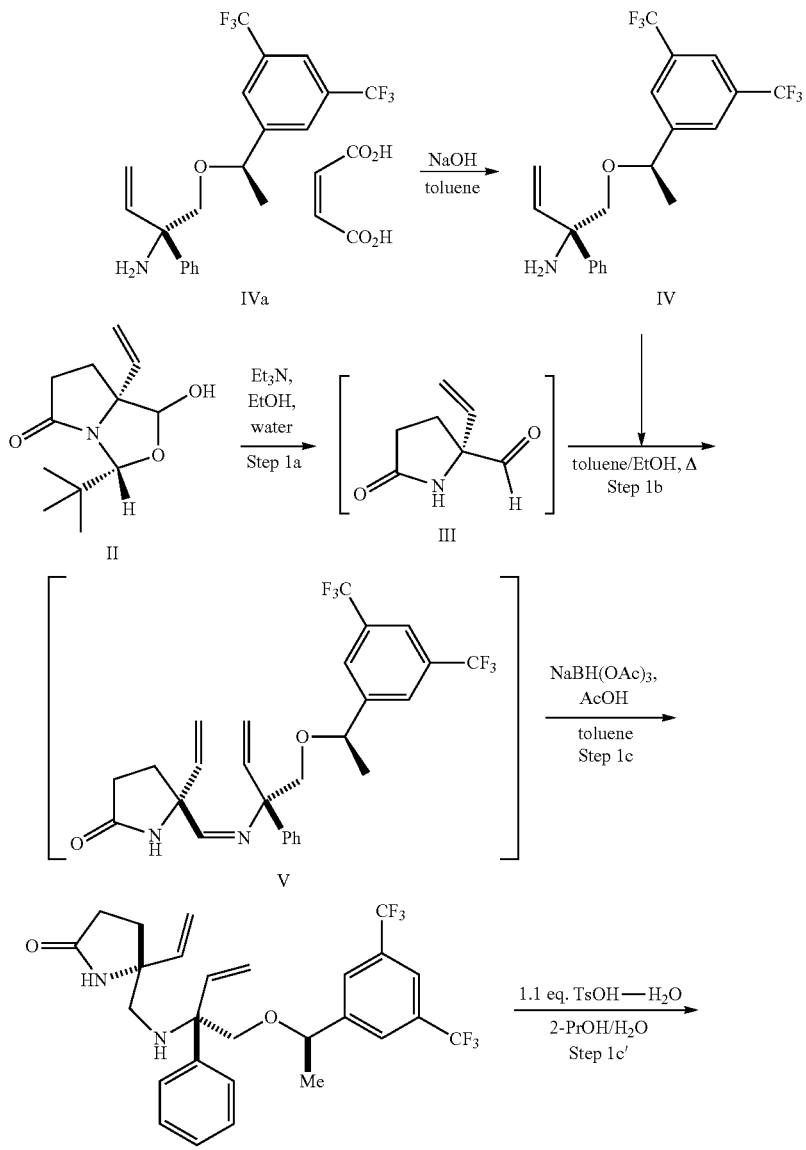

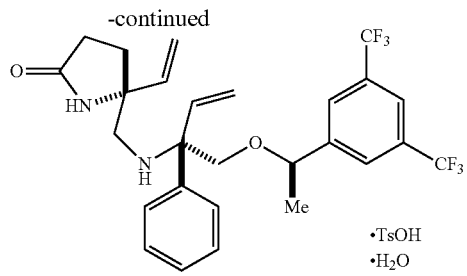
·TsOH
·H₂O

In some embodiments, it is preferred to provide the compound of Formula III by carrying out Step 1a, wherein the compound of Formula II is converted to the compound of Formula III by treatment with a base, for example, a lower alkyl amine, for example, a tertiary amine, for example, triethylamine, diisopropylethylamine, or tributylamine, in a solvent that is miscible with water, for example, a lower alcohol (that is, having from about 1 to about 6 carbon atoms), for example ethanol, methanol, isopropanol, butanol or mixtures thereof, at a temperature of from about 0° C. to about 80° C., preferably from about 10° C. to about 60° C., more preferably from about 20° C. to about 30° C., and for a period of from about 3 hours to about 10 hours.

In Step 1b, the compound of Formula III, for example, as the mixture from Step 1a, is added to a solution of the free base of Formula IV and heated to react the two. After addition the mixture is heated to reflux and water generated in the reaction is removed via azeotropic distillation to drive the reaction. In some embodiments, the freebase of Formula IV is prepared from a salt of Formula IVa by treating the salt of Formula IVa with a water soluble base, for example, NaOH dissolved in a low polarity solvent, for example, toluene or a non-polar solvent, for example, xylenes, or mixtures of the two.

In some embodiments, in Step 1c, it is preferred to reduce the product of Step 1b is with a source of hydride, for example, metal hydride reducing reagents, for example, sodium borohydride, sodium cyanoborohydride, or sodium triacetoxyborohydride, in the presence of an acid, for example, acetic acid, trifluoroacetic acid, phosphoric acid, methanesulfonic acid or trifluoromethanesulfonic acid and mixtures thereof to obtain the free base of Formula VI. In some embodiments it is preferred to carry out the reaction in toluene, acetonitrile, 1,2-dichloroethane, tetrahydrofuran, ethyl acetate, isopropyl acetate, or mixtures of two or more thereof. In some embodiments it is preferred to carry out the reaction at a temperature of from about 0° C. to about 80° C., preferably from about 10° C. to about 60° C., more preferably from about 15° C. to about 25° C. In some embodiments it is preferred to carry out the reaction for a period of from about 2 hours to about 10 hours. After obtaining a free base of Formula VI, it is converted (step 1c') to a salt compound of Formula VIa by treatment with an acid reagent, for example, p-toluene sulfonic acid, methanesulfonic acid, trifluoromethanesulfonic acid, trifluoroacetic acid, HCl, HBr, or sulfuric acid. In some embodiments it is preferred to carry out the conversion to a salt compound of Formula VIa in a water-miscible solvent, for example, alkyl alcohol having from about 1 to about 6 carbon atoms, for example, methanol, ethanol, propanol, isopropanol, or butanol and its isomers, or a mixture of two or more thereof, and thereafter isolate the salt product.

In Step 2, the salt compound of Formula VIa is converted to a free base, which is then cyclized with a ring closing metathesis catalyst, and the resultant product is converted again to a salt and isolated.

The ring closing metathesis catalysts are preferably those containing a metal with a carbene ligand, for example, the catalyst of Formula XX:

XXa
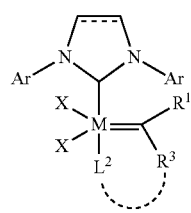

XXb
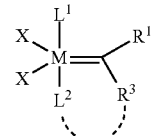

XXd
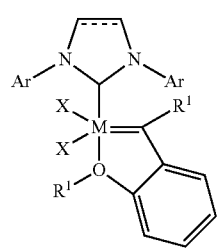

where the metal (M) is preferably a transition metal with a formal oxidation state providing 8 "d" orbital electrons (a group 8 transition metal, for example, ruthenium, palladium or iridium) or a group 6 transition metal, for example, molybdenum; (X) is a conjugate base of a strong acid, preferably X is: a sulfonate moiety, for example, tosylate; or halogen moiety, for example, chloride; (L¹) is a sigma-bonded carbon ligand with substantial Pi-backbonding capability, for example, as shown in the catalyst of Formula XXa, an imidazolidine ligand

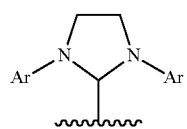

(wherein Ar is an aryl moiety, for example benzyl, phenyl or mesityl (2,4,6-trimethyl phenyl)moiety), L² is a phosphine ligand, for example (Cy$_3$P), or, as indicated, L$^2$ is optionally bonded to R$^3$, illustrated by the semicircular dotted line between L$^2$ and R$^3$, when L$^2$ is bonded to the carbene moiety via R$^3$, it forms a bidentate ligand, and L$^2$ is a chelating moiety, for example, an oxygen, phosphorous, or nitrogen moiety, for example, the oxygen moiety in the isoproxybenzylidene bidentate ligand shown in the catalyst of Formula XXd, R$^1$ is independently selected from aryl, alkyl, or hydrogen, and R$^3$ is an alkyl or phenyl moiety, or when R$^3$ is not bonded to L$^2$, R$^3$ may be hydrogen.

Suitable ring-closing metathesis catalysts are commercially available, for example: (i) the catalysts described as "Grubbs' First generation catalyst" in U.S. Pat. No. 6,215,019 and that described as "Grubbs' Second Generation catalysts" in published PCT Application Nos. WO 99/51344 and WO 00/71554 and the catalysts described as "Hoveyda-Grubbs' First and Second Generation catalysts" in published PCT Application No. PCT/US01/24955, both available from Materia; (ii) Zhan's catalyst described in published international application publication no. WO 2007/003135), available from Zannan Pharma; and (iii) Grela's catalyst described in published international application publication no. W)2004/035596, available from Boehringer-Ingelheim. In some embodiments of the present invention it is preferred to use a catalyst having: (i) a chelating isoproxybenzylidene ligand; and (ii) a bismestiylene-substituted N-heterocyclic carbene ligand, for example, the Hoveyda-Grubbs' Second Generation Catalyst.

In some embodiments it is preferred to employ a catalyst of the formula:

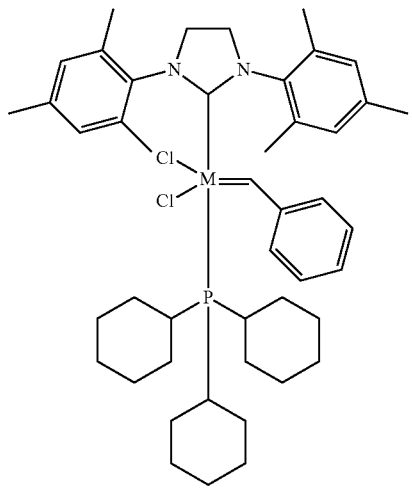

In some embodiments it is preferred to employ a catalyst of the formula:

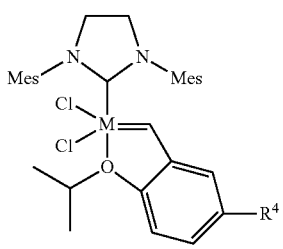

where R$^4$ is "H—", a nitro moiety (—NO$_2$), or a sulfonamide moiety (—SO$_2$N(R$^5$)$_2$, wherein R$^5$ is an alkyl moiety of 10 carbon atoms or less).

With reference to Scheme 1, Step 2, in some embodiments it is preferred to use a reaction mixture loading of the ring-closing metathesis catalyst (catalyst loading) in an amount of from about 100 mol % to about 0.1 mol %, more preferably the catalyst is used in an amount of from about 20 mol % to 0.1 mol %, and more preferably about 10 mol % to about 0.5 mol %, relative to the amount of the compound of Formula V initially present in the reaction mixture. As mentioned above, the addition of acid to the reaction mixture in Step 2, for example, 4-methylbenzenesulfonic acid monohydrate or toluenesulfonic acid, can reduce the reaction mixture catalyst loading required to achieve complete, or nearly complete, conversion of the substrate under given reaction conditions. Table I, below, illustrates the results obtained by adding various amounts of p-toluenesulfonic acid to the reaction mixture and observing the amount of substrate conversion as a function of catalyst loading with and without added acid. In some embodiments where acid is added to reduce catalyst loading it is preferred to add acid in an amount of from about 0.01 equivalents (eq.) to about 2 equivalents (eq.) relative to the amount of substrate initially present in the reaction mixture, more preferably, acid is added in an amount of from about 0.1 eq. to about 1.8 eq., and more preferably acid is added in an amount of from about 0.2 eq. to about 1.5 eq. relative to the amount of substrate initially present in the reaction mixture.

Without wanting to be bound by theory, the inventors believe that best results respecting the use of added acid in Step 2 for the reduction of catalyst loading will be achieved by adding to the reaction mixture an acid possessing a pKa≤6.5, which is the calculated pKa of intermediate IV. Various types of acid are believed to be useful for reducing the required catalyst loading to achieve high conversion of the substrate, for example, but not limited to: (i) mineral acid, for example HCl, HBr, HI, phosphoric acid, or sulfuric acid or mixtures thereof; and (ii) organic acid, for example, acetic acid, trifluoroacetic acid, methanesulfonic acid, trifluoromethanesulfonic acid, benzenesulfonic acid, p-toluenesulfonic acid, p-nitrobenzenesulfonic acid, halogen-substituted benzenesulfonic acid, or heteroaromatic sulfonic acid, or mixtures thereof.

TABLE I

| Conversion vs. Catalyst Loading vs. TsOH Charged | | |
|---|---|---|
| Catalyst Loading (mol %) | Additional TsOH Added (mol %) | Reaction Conversion (% of VII/VI) |
| 5 | 0 | 85-90 |
| 5.5-7 | 0 | 90-100 |
| >7 | 0 | 100 |
| 1 | 20 | 57 |
| 5 | 20 | 100 |
| 3 | 60 | 100 |
| 5 | 60 | 100 |
| 5 | 100 | 100 |
| 2 | 100 | 93-100 |
| 1 | 100 | 88 |
| 1.5 | 150 | 98-100 |
| 1 | 150 | 98 |
| 0.5 | 150 | 76 |
| 1 | 200 | 44 |

With reference to Table I, cyclization reactions in accordance with Step 2 of Scheme I (above) were run employing from 0 to about 2 mole equivalents (eq.) of added acid relative to the amount of substrate to be cyclized. These data show that adding acid to the reaction mixture in Step 2 can reduce by a factor of more than 4.5 the catalyst loading required in the reaction mixture to achieve a high percentage conversion of the substrate. Accordingly, where loadings of 7 mol. % or more were needed to achieve nearly 100% substrate conversion without added acid, conversions approaching 100% of substrate could be achieved using a catalyst loading of 1.0 mol. % in conjunction with 150 mol. % additional acid in the reaction mixture.

In some embodiments it is preferred to carry out the ring-closing reaction of Step 2 in an anhydrous, degassed (for example, using $N_2$) reaction medium comprising a non-coordinating medium polarity solvent, for example, toluene, trifluorotoluene, chlorobenzene, benzene, xylene(s), chloroform, dichloromethane, or dichloroethane. In general, the reaction is carried out at atmospheric pressure or a pressure slightly elevated above atmospheric pressure. In some embodiments it is preferred to carry out the ring-closing metathesis reaction by dissolving the catalyst in a solvent which is the same as, or similar to, the reaction solvent and adding the catalyst solution slowly over a period of about 30 minutes while maintaining the temperature of the reaction mixture within a temperature range of from about 20° C. to about 100° C., preferably from about 30° C. to 90° C. and more preferably from about 60° C. to about 80° C.

In some embodiments, at the end of the cyclization reaction it is preferred to remove the metal from the catalyst using the process described in Scheme 4, i.e., the product of the ring-closing procedure is treated with an aqueous solution of a reducing reagent and the resultant metal species is extracted into the aqueous layer. Suitable reducing reagents include, but are not limited to, inorganic reagents, for example, sodium bisulfite, sodium metabisulfite, sodium thiosulfite, sodium formate, sodium borohydride and its derivatives.

In some embodiments employing the process of Scheme 4 to remove metal from the metathesis catalyst, it is preferred to employ also in the reaction mixture a phase transfer catalyst (PTC) in an amount of from about 0.05 mol % of PTC relative to the amount of reducing reagent employed to about 200 mol % of PTC relative to the amount of reducing reagent employed, preferably PTC is employed in an amount which is from about 0.1 mol % to about 100 mol % relative to the amount of reducing reagent employed. Suitable phase transfer catalysts for use in the process include, but are not limited to, quaternary ammonium salts of the Formula ($R*_4N^+X^-$) wherein "R*" is an alkyl group, as defined herein, and "X" is an anion, preferably "X" is $Cl^-$, $Br^-$, $I^-$, $F^-$, or $NO_3^-$. The inventors have surprisingly found that when the process is carried out in the presence of a suitable phase transfer catalyst, the PTC permits the reduction to proceed to completion at either a lower temperature, for example, as low as 25° C., within a shorter period of time, for example, in less than 1 hour, or depending upon the temperature regime selected, both the reaction period and the reaction temperature can be reduced over that required to achieve a complete reduction in the absence of a phase transfer catalyst.

In some embodiments it is preferred to convert the cyclized product from which the catalyst has been removed to a salt by treatment of the reaction mixture containing the cyclized product with a reagent comprising: (i) a mineral acid, for example, HCl, HBr, HI, $H_3PO_4$, or $H_2SO_4$; (ii) an organic acid or substituted organic acid, for example, Maleic Acid, Fumaric Acid, Tartaric Acid or trifluoroacetic acid; (iii) a sulfonic acid or substituted sulfonic acid, for example, methanesulfonic acid, trifluoromethanesulfonic acid, benzenesulfonic acid, p-Toluenesulfonic acid, or p-nitrobenzenesulfonic acid. In some embodiments it is preferred to prepare the HCl salt of the compound of Formula VI.

With reference to Scheme I, in Step 3, the salt of Formula VII is converted to the free base form. In some embodiments it is preferred to accomplish the conversion by treating the compound of Formula VII with a base, for example, NaOH, KOH, NaOR (where "R" is an alkyl group containing from about 1 to about 12 carbon atoms). In some embodiments the conversion of the compound of Formula VII in Step 3 is carried out in a reaction solvent comprising a low polarity organic solvent, for example, toluene, Xylene, ethers (for example, diethyl ether and methyl t-butyl ether), to obtain the free base of VII, and subsequently reduce the free base to the compound of Formula VIII by hydrogenation, for example by treatment with hydrogen in the presence of a hydrogenation catalyst, for example, palladium on carbon, platinum on carbon, palladium oxide, ruthenium, or Wilkinson's catalyst, or mixtures thereof. In some embodiments it is preferred to carry out Step 3 in a low polarity, organic solvent, for example, toluene or Xylene, or in a polar organic solvent, for example alcohols (C1 to C12 linear or branched alkyl), or ethers, or in water, or a mixtures of two or more thereof. In some embodiments, after the hydrogenation reduction is complete, the catalyst employed in Step 3 is removed from the reaction mixture, for example, by filtration, and the product compound in the reaction mixture is then treated with an acid to make the corresponding salt, for example, in embodiments where the product compound is treated with HCl at this step, the compound of Formula VIII (Scheme I) is obtained as the hydrochloride hydrate.

The inventor's have surprisingly found that alternatively, with reference to Scheme I, above, the tetrahydropyridine salt compound of Formula VII can be directly reduced to yield the corresponding amine-salt compound. When the compound of Formula VII is a hydrochloride salt, reduction of the salt compound of Formula VII yields the hydrochloride hydrate compound of Formula VIII directly without having to generate the intermediate free-base form of the tetrahydropyridine, the compound of Formula VIIb. In some embodiments employing direct reduction of the tetrahydropyridine salt compound of Formula VII, preferably after the reduction reaction is complete, the catalyst employed in the reduction is removed from the reaction mixture by mechanical means, for example, by filtration, and the resultant amine salt is recovered from the filtrate.

For carrying out the reduction of a salt compound of Formula VII directly without first providing the free-base form of the tetrahydropyridine, the inventors have surprisingly found that the reaction is preferably carried out in a solvent which is: (i) a low polarity organic solvent, for example, toluene or xylene or a mixture thereof; (ii) a polar organic solvent, for example, alcohols comprising from about 1 carbon atom to about 12 carbon atoms or a mixture of two or more thereof; (iii) organic ethers comprising from about 2 to about 12 carbon atoms or a mixture of two or more thereof; and (iv) water, or mixtures of any two or more thereof.

Suitable methods for reducing the salt-form of the tetrahydropyridine compound to the corresponding cyclohexylamine include treatment of the compound of Formula VII with hydrogen in the presence of a hydrogenation catalyst Suitable hydrogenation catalysts include, for example, palladium on carbon, palladium oxide, platinum on carbon, ruthenium and Wilkinson's catalyst or mixtures of two or more thereof.

In some embodiments, following Step 3 of Scheme I, it is preferred to carry out Step 4, recrystallizing the product of Step 3 from an alcohol/water solution, thereby providing a desirable crystalline form of the compound of Formula Ia. Suitable alcohol solvents useful in carrying out Step 4 include, but are not limited to, alcohols having from about 1 to about 12 carbon atoms, or a mixture of two or more thereof. Alternatively to recrystallization, the compound of Formula VIII can be suspended in toluene, the suspension extracted with aqueous NaOH, and then treated with HCl to precipitate compound of Formula Ia.

As mentioned above, in some embodiments of the present invention it is preferred to prepare the intermediate of Formula IV using the process illustrated in Scheme 2. In some embodiments employing the process of Scheme 2 to provide the compound of Formula IV, it is preferred to use the conditions and parameters illustrated below in Scheme 2ab in carrying out Scheme 2.

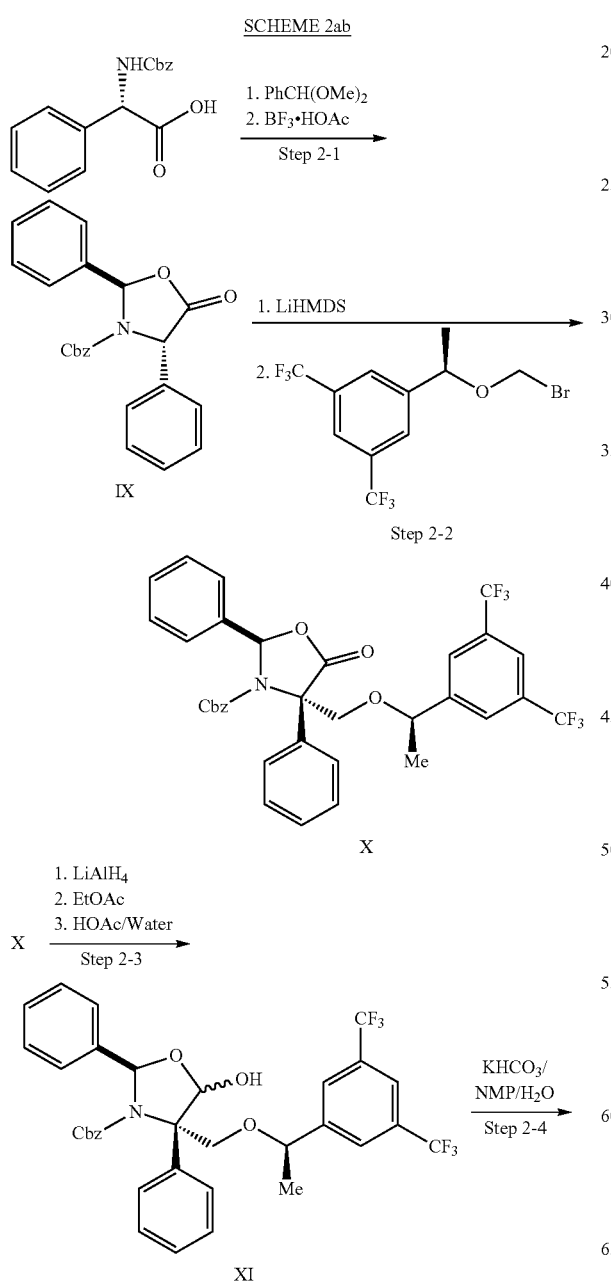

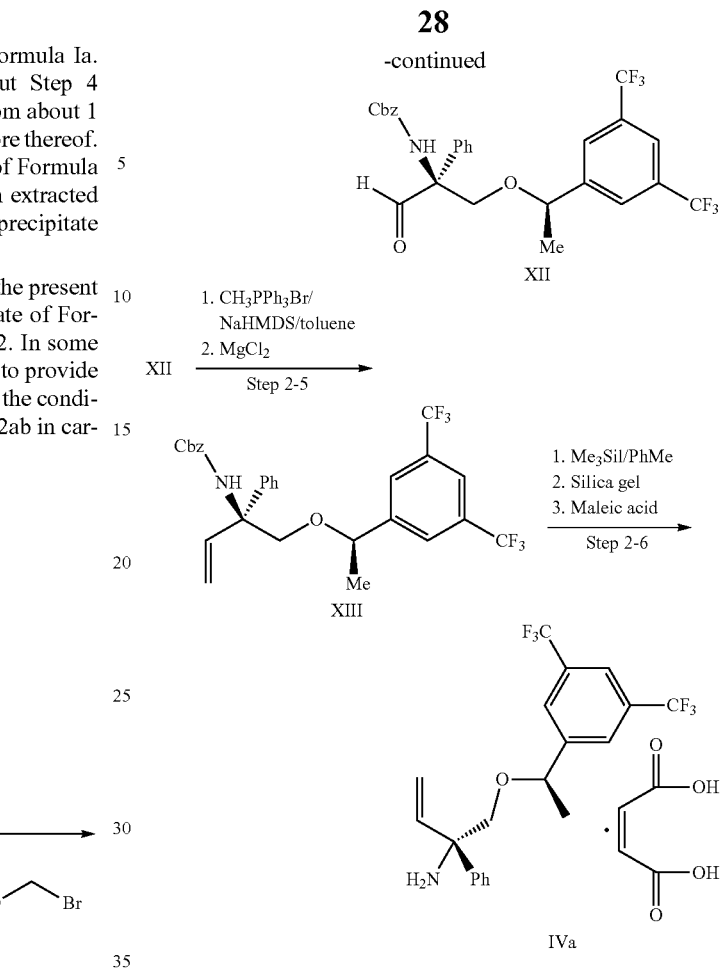

In the process of Scheme 2ab, Steps 2-1 to 2-3 are described in the above-mentioned U.S. Pat. No. 7,049,320 (the '320 patent) the Examples, columns 43 to 44, compounds 1 to 3, and removal of the triphenylphosphine oxide resulting from carrying out step 2-5.1 shown in Scheme 2ab is described on pages 4 to 5 of European published application No. EP 0850902.

In some embodiments it is preferred to carry out Step 2-4 of Scheme 2ab using a base, for example, $KHCO_3$ or $NaHCO_3$ in a solvent, for example, NMP water, a mixture of acetonitrile and water, or a mixture of acetone and water. In some embodiments it is preferred to stir the reaction mixture while maintaining the reaction mixture at a temp of from about 0° C. to about 60° C., preferably from about 5° C. to about 50° C., more preferably from 15° C. to about 25° C., and after a period of agitation, heat the reaction mixture up to a temperature of less than about 90° C., preferably to a temperature of less than about 70° C., more preferably, of from about 45° C. to about 55° C., followed by cooling the reaction mixture to ambient temperature (typically about 25° C.) and extracted the ambient temperature reaction mixture with an organic solvent, for example, methyl t-butyl ether (MTBE), ethyl acetate, isopropyl acetate, toluene, Xylene or a mixture of two or more thereof.

With further reference to Scheme 2ab, Step 2-5 is carried out by adding the product of Step 2-4 to a mixture of $Ph_3PCH_3X$ (X=Cl. Br, or I) and sodium or lithium hexamethyldisilizane or lithium diisopropylamide, sodium or potassium alkoxide in an organic solvent, for example, toluene, THF, MTBE at a temperature range from −20 to 60° C., preferably from 5 to 40° C., more preferably from 10 to 25° C.

The reaction mixture is warmed to room temperature and stirred, then cooled to range from −30 to 40° C., preferably from −20 to 30° C., more preferably from −10 to 20° C., and quenched with dilute acetic acid and washed with sodium bicarbonate solution. The product is treated with MgCl₂ and stirred at room temperature, then treated with silica gel. Filtration of solid gives the compound of Formula XIII.

In step 2-6, the crude product Formula XIII is treated with TMSI (iodotrimethylsilane) and quenched with an alcohol having from about 1 to about 12 carbon atoms, thereby providing (with reference to Scheme I, step 1b) the free base of Formula IV. As illustrated in Step 2-6 of scheme 2ab, the free base of Formula IV provided is treated with an acid, for example, maleic acid, hydrochloric acid, and hydrobromic acid, to form the corresponding salt, preferably maleic acid is used, thereby providing the corresponding maleate salt compound of Formula IVa. In some embodiments, it is preferred to cyrstallize the salt thereby provided from toluene and an anti solvent, for example, hexane, heptane or octane, to provide a crystalline form of the salt.

As mentioned above, in some embodiments of the present invention it is preferred to prepare the intermediate of Formula II using the process illustrated in Scheme 3. In some embodiments employing the process of Scheme 3 to provide the compound of Formula II, it is preferred to use the conditions and parameters illustrated below in Scheme 3ab in carrying out Scheme 3.

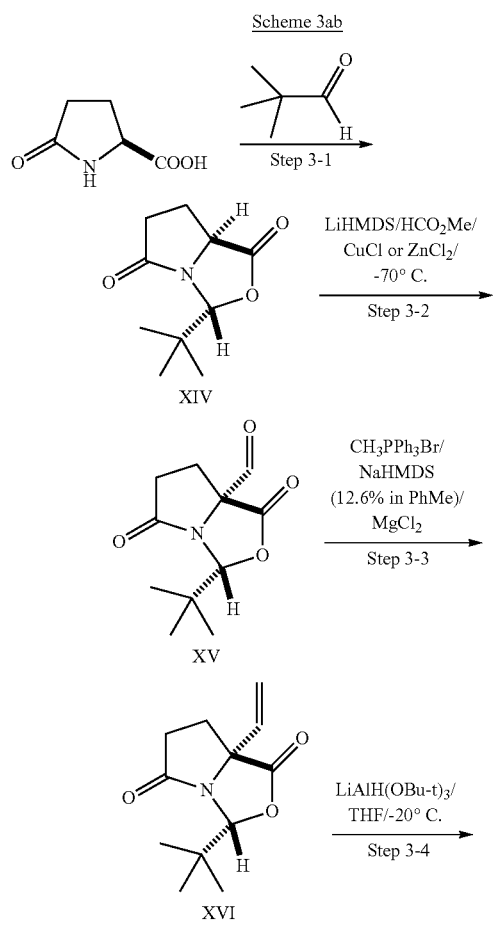

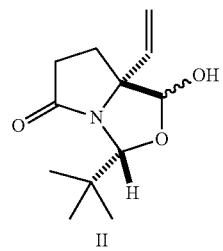

With reference to Scheme 3ab, in some embodiments it is preferred to carry out Step 3-1 using one of several methods:
a) refluxing pyroglutamic acid with diethylene glycol dimethyl ether, trimethylacetaldehyde and a strong acid, for example methanesulfonic acid; or
b) heating pyroglutamic acid with trimethylacetaldehyde and a strong acid, for example, methanesulfonic acid; or
c) refluxing pyroglutamic acid with hexamethyl disilizane, then reacting the product with trimethylacetaldehyde and methanesulfonic acid; or
d) heating pyroglutamic acid and triethylamine with chlorotrimethylsilane, and then reacting the product with trimethylacetaldehyde and a strong acid, for example, methanesulfonic acid; or
e) adding trifluoroacetic anhydride to a mixture of pyroglutamic acid, trimethylacetaldehyde and a strong acid and maintaining the temperature from about 50° C. to about 100° C. until the reaction is complete.

In method (a), the compound of Formula XIV is prepared by refluxing pyroglutamic acid in diethylene glycol dimethyl ether solvent, in the presence of trimethylacetaldehyde and a strong acid. In some embodiments it is preferred for the strong acid to be trifluoroacetic acid, phosphoric acid, sulfuric acid, methanesulfonic acid, trifluoromethanesulfonic acid, benzenesulfonic acid, p-toluenesulfonic acid or p-nitrobenzenesulfonic acid. In some embodiments of method (a) refluxing with pyroglutamic acid is carried out in the presence of a co-solvent, for example, toluene, Xylene, cyclohexane, THF, or a mixture of two or more thereof, at refluxing temperature employing a Dean Stark water-removal apparatus on the refluxing apparatus until the reaction is complete.

In method (b), a mixture of pyroglutamic acid with trimethylacetaldehyde and a strong acid, without the diethylene glycol dimethyl ether solvent used in method (a) is heated in an apparatus permitting, water removal, for example, a Dean Stark water-removal apparatus. In method (b), as in method (a), in some embodiments it is preferred to select as a strong acid trifluoroacetic acid, phosphoric acid, sulfuric acid, methanesulfonic acid, trifluoromethanesulfonic acid, benzenesulfonic acid, p-toluenesulfonic acid or p-nitrobenzenesulfonic acid. In some embodiments the mixture is heated to reflux, typically from about 100° C. to about 120° C., while water is azeotropically distilled off through the trap, and reflux is continued until water removal is complete. On a bench-scale equipment this is typically accomplished in about 14.5 hours.

In method (c), pyroglutamic acid and hexamethyl disilizane in a solvent which is preferably dioxane, diglyme, toluene or N-methylpyrrolidinone (NMP) are heated to reflux for a period of from about 6 hours to about 12 hours. Trimethylacetaldehyde and a strong acid, for example, trifluoroacetic acid, phosphoric acid, sulfuric acid, methanesulfonic acid, trifluoromethanesulfonic acid, benzenesulfonic acid, p-toluenesulfonic acid or p-nitrobenzenesulfonic acid are added to the product, and the resultant mixture is heated to 90° C. for a period of from about 4 hours to about 12 hours.

In method (d), chlorotrimethylsilane is added to a mixture of pyroglutamic acid and triethylamine in toluene while keeping the temperature under 30° C., and then the mixture is heated to reflux until the silylation is completed. The resultant trimethylsilyl-protected compound is added to a solvent, for example, N-methyl-2-pyrrolidone, or acetonitrile and treated with trimethylacetaldehyde and a strong acid, for example, trifluoroacetic acid, phosphoric acid, sulfuric acid, methanesulfonic acid, trifluoromethanesulfonic acid, benzenesulfonic acid, p-toluenesulfonic acid or p-nitrobenzenesulfonic acid, maintaining the temperature of the reaction mixture in a temperature range of from about 50° C. to about 100° C., preferably from about 60° C. to about 90° C., more preferably, from about 70° C. to about 85° C. until the reaction is complete, typically a period of from about 18 hours to about 24 hours.

In method (e), a mixture of pyroglutamic acid, trimethylacetaldehyde, and a strong acid is prepared and trifluoroacetic anhydride is added to it. In some embodiments the strong acid is selected from: organic acid, for example, trifluoroacetic acid; mineral acid, for example, phosphoric acid or sulfuric acid; sulfonic acid, for example, methanesulfonic acid, trifluoromethanesulfonic acid, benzenesulfonic acid, p-toluenesulfonic acid or p-nitrobenzenesulfonic acid. In some embodiments it is preferred to carry out the reaction in an organic solvent, for example, toluene or N-methyl-pyrrolidone. In some embodiments it is preferred to maintain the reaction mixture at a temperature of from about 70° C. to about 95° C., more preferably the temperature is maintained at from about 80° C. to about 95° C. In general the reaction mixture is maintained in the desired temperature range until the reaction is complete, typically about 5 to about 10 hours.

In Step 3-2, the compound of Formula XIV is mixed with: (i) a solvent which is preferably 1,3-dimethyl-2-imidazolidinone (DMI) or tetrahydrofuran, (ii) methyl formate or ethyl formate; and (iii) optionally a Lewis acid, for example, CuCl or ZnCl$_2$. When a Lewis acid is employed, typically the Lewis acid is added in amounts of up to about 1 eq. relative to the amount of the compound of Formula XIV employed. In some embodiments a Lewis acid is employed in this step to increase yield and simplify workup of the reaction mixture. Following the addition of the constituents, the reaction mixture is cooled to a temperature of from about [−100]° C. to about [−55]° C., then, maintaining the temperature of the reaction mixture, to the reaction mixture is added lithium bis(trimethylsilyl)amide (LiHMDS) followed by chlorotrimethylsilane (TMSCl). After addition is complete, the reaction mixture is warmed to a temperature of from about 0° C. to about [+10]° C. and combined with an aliquot of a citric acid or acetic acid solution. The resultant intermediate is treated with trifluoroacetic acid to obtain the pyrrolo[1,2-c]oxazole-7a-carbaldehyde of Formula XV.

In Step 3-3, the carbaldehyde of Formula XV is converted to the 7a-vinyl-dihydro-pyrrolo[1,2-c][1,3]oxazole-1,5-dione of Formula XVI by a Wittig reaction, for example by treating it with methyltriphenylphosphonium halide (Halide=Cl. B, or I) and sodium or lithium hexamethyldisilizane or lithium diisopropylamide, sodium or potassium alkoxide in an organic solvent, preferably toluene, THF, or MTBE, at a temperature range from about [−20]° C. to about [+60]° C., preferably from about [−10]° C. to about [+30]° C., more preferably from about [+5]° C. to about [+15]° C., then the reaction mixture is quenched by adding NaCl and acetic acid. The product is treated with MgCl$_2$ and the MgCl$_2$-triphenylphosphine oxide complex thus formed is separated from the reaction mixture by filtration. The product remaining in the reaction mixture is crystallized from toluene and heptane to give the compound of Formula XVI.

In Step 3-4, the compound of Formula XVI is dissolved in an ether solvent which is preferably tetrahydrofuran or MTBE, or in a low polarity organic solvent, for example, toluene. The reaction mixture is maintained at a temperature of from about [−40]° C. to about 0° C., preferably at a temperature of from about [−30]° C. to about [−5]° C., more preferably at a temperature of from about [−25]° C. to about [−15]° C., and then the reaction mixture is treated with lithium tri(t-butoxy)aluminum hydride, lithium aluminum hydride, or Lithium diisobutylaluminium hydride and the temperature is raised to a temperature of from about [−10° C. to about [+10]° C. over a period of from between about 10 hours to about 16 hours and maintained until the reaction is complete. When the reaction is completed, the reaction mixture is quenched with an acetate solvent, which is preferably ethyl acetate, methyl acetate, or isopropyl acetate, and then contacted consecutively with aliquots of an acid, preferably glacial acetic acid or trifluoroacetic acid, and then an aliquot sodium sulfate decahydrate to obtain the compound of Formula II.

For the intermediate compounds claimed per se, i.e.

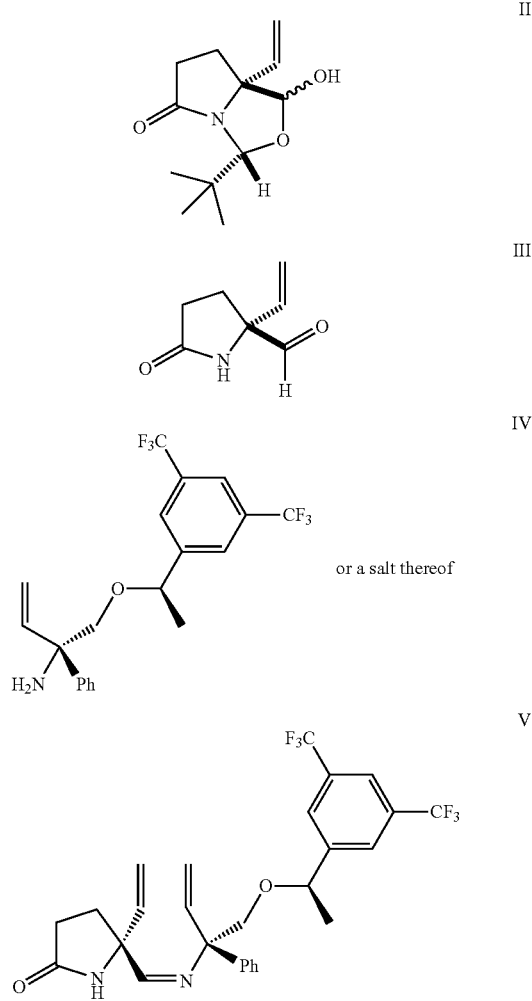

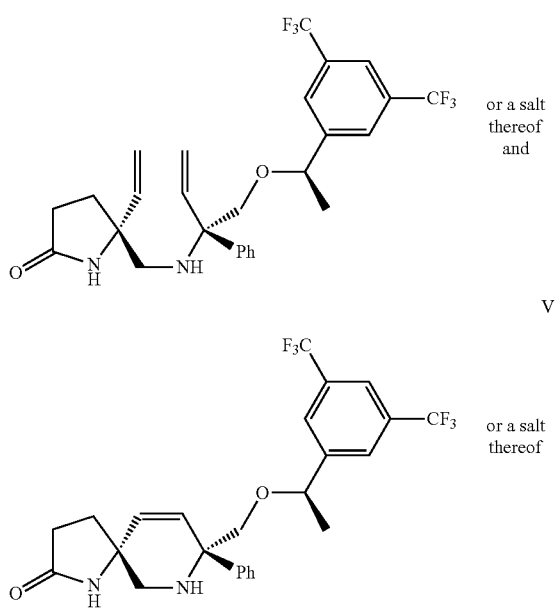

In some embodiments it is preferred to isolate compound IV as either a maleate salt, including hydrates thereof, or as a hydrochloride salt, including hydrates thereof. In some embodiments the compounds of Formulae VI and VII are preferably isolated as a hydrochloride salt or a 4-methyl-benzenesulfonic acid salt, more preferably the hydrate of a 4-methyl-benzenesulfonic acid salt.

As mentioned above, at the conclusion of Step 2 of Scheme 1, the process illustrated in Scheme 4, above, can be employed to remove metal from the reaction mixture of a ring closing metathesis reaction, allowing the metal to be recycled and providing the product intermediate compound substantially free of contamination from the metathesis catalyst.

With reference to Scheme 4, illustrated above herein, the inventors have surprisingly found that the metathesis catalyst can be removed from the reaction mixture when the ring-closing reaction is complete by treating the reaction mixture containing the metathesis catalyst with a reducing reagent that reacts with the metathesis catalyst. The process described in Scheme 4 comprises reducing the catalyst in the reaction mixture which comprises a water-immiscible solvent by contacting the reaction mixture with an aqueous solution containing a reducing reagent, wherein, the reduction product of the metathesis catalyst is either soluble in the aqueous layer, and thus is physically separated from the organic layer using the immiscibility of the two layers, for example, by separation or decantation, or is insoluble in either the organic or aqueous layer, and thus physically separated from the reaction mixture by filtration.

For carrying out the metathesis reduction reaction described in Scheme 4, above, suitable reducing reagents include: (i) one or more inorganic salt compounds, which are $Na_2S_2O_5$, $Na_2SO_3$, $NaSO_3H$, $NaOC(O)H$, or $NaH_2PO_3$; (ii) a phosphorous acid, for example, $H_3PO_2$; (iii) one or more metal hydride compounds, for example, sodium hydride, sodium borohydride, or lithium aluminum hydride; (iv) hydrogen in the presence of a reduction catalyst, for example, palladium on carbon; (v) an organic reducing reagent, for example, ascorbic and oxalic acids; (vi) hydrogen peroxide; or (vii) one or more metals capable of carrying out a reduction reaction, for example, copper, zinc, iron or magnesium.

In some embodiments it is preferred to include in the reaction an inorganic salt compound which can function in the reaction as a phase transfer catalyst (PTC), for example, a quaternary ammonium salt, for example $(CH_3(CH_2)_3)_4N^+X^-$, wherein X is preferably a chloride, bromide, iodide, fluoride, bisulfate ($HSO_4^-$), sulfate ($SO_4^{-2}$), or nitrate anion. The inventors have found surprisingly that including a PTC can permit the reaction to be carried out at a temperature of as low as about 20° C., whereas, without a PTC the reaction required a temperature of about 40° C. to proceed. Moreover, the presence of a PTC in the reaction can significantly reduce the time required to complete the reaction at a particular temperature, for example, reducing to a period of about 6 minutes a reaction requiring a reaction time for a particular temperature of about 1 hour.

Accordingly, in some embodiments utilizing the reaction process of Scheme 4 to remove the metathesis catalyst used for ring-closure in the synthesis, it is preferred to employ, as a water-immiscible solvent comprising the reaction mixture toluene, trifluorotoluene, chlorobenzene, benzene, xylene(s), dichloromethane, or dichloroethane or mixtures of two or more thereof. In some embodiments utilizing the reaction process of Scheme 4 to remove the metathesis catalyst used for ring-closure in the synthesis, it is preferred to carry out the reduction reaction at a temperature of from about 20° C. to about 100° C. In some embodiments utilizing the reaction process of Scheme 4 to remove the metathesis catalyst used for ring-closure in the synthesis, it is preferred to run the reaction for a period of from about 0.1 hour to about 24 hours. Generally, when this method is employed to remove the metathesis catalyst, the reaction is continued until all of the metathesis catalyst has been reduced. At the end of the reduction reaction the reduced metal, typically in the form of an $ML_2$ complex, is either soluble, and so in the course of the reaction is extracted into the aqueous solution comprising the reducing reagent, or is insoluble in either the organic or aqueous layers, and therefore precipitates from the organic and aqueous mixture.

In some embodiments utilizing the reaction process of Scheme 4 to remove the metathesis catalyst used for ring-closure in the synthesis, where "M" of the metathesis catalyst, for example, the metathesis catalyst of Formula XXa, is ruthenium, it is preferred to employ $Na_2S_2O_5$, $Na_2SO_3$ or Pd on carbon in the presence of hydrogen as the reducing reagent. In some embodiments utilizing the reaction process of Scheme 4 to remove the metathesis catalyst used for ring-closure in the synthesis, where "M" of the metathesis catalyst, for example, the metathesis catalyst of Formula XXa, is ruthenium, it is preferred to include also a PTC as described above, more preferably, in processes wherein "M" of the metathesis catalyst is ruthenium, it is preferred to employ $[(CH_3(CH_2)_3)_4N^+(HSO_4^-)]$ or $[(CH_3(CH_2)_3)_4N^+]_2(SO_4^{-2})]$ as the phase transfer catalyst.

It will be appreciated that the novel method presented above for separating a metathesis catalyst from the reaction mixture at the end of the reaction can be used to cleanly remove a metal metathesis catalyst from other reactions employing such catalysts so long as the reduction product containing the metal is either insoluble in the mixed-phase reaction product obtained after reduction or is soluble in the aqueous phase of the mixed-phase reaction product.

There follows examples illustrating the processes of the invention. Unless otherwise specified, all reagents are articles of commerce, laboratory grade, and used as received.

EXAMPLE 1

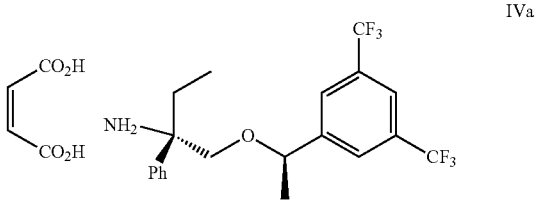 [SMILES: O=C(O)/C=C\C(=O)O ; CC[C@@](N)(CO[C@H](C)c1cc(C(F)(F)F)cc(C(F)(F)F)c1)c1ccccc1]

Preparation of [(1S)-1-({(1R)-1-[3,5-Bis(trifluoromethyl)phenyl]ethoxy}methyl)-1-phenylprop-2-enyl]amine, monomaleate Step 1:

To a solution of the compound of Formula XI (prepared as described in WO 2003/054840) (100.0 g, 154.9 mmol) in NMP (200 mL) at RT were sequentially added $KHCO_3$ (4.6 g, 45.9 mmol) and water (3 mL, 166.7 mmol). The resulting mixture was stirred vigorously for 16 h at 20° C. The temperature was then raised to 50° C. and the reaction was stirred for another 2 h. After the reaction was cooled back to RT, 200 mL of water was added. The resulting solution was extracted with TBME (2×200 mL). The combined organic layers were sequentially washed with a solution of 14% $NaHSO_3$ and 7% AcOH in water (2×100 ml), a saturated aq. $NaHCO_3$ solution, and brine. The organic layer was dried ($Na_2SO_4$), filtered and concentrated in vacuum. The crude compound of Formula XII was carried through to the next stage without further purification.

$^1$H NMR (DMSO-$d_6$, 600 MHz) δ 9.53 (s, 1 H), 8.36 (s, 1H), 8.00 (s, 1H), 7.89 (s, 1H), 7.34 (m, 10H), 5.09 (dd, 2H), 4.72 (dd, 1H), 4.03 (d, 1H), 3.90 (d, 1H), 1.34 (d, 3H).

Step 2:

To a slurry of $Ph_3PCH_3Br$ (78.0 g, 217.0 mmol) in toluene (200 mL) was added NaHMDS (13% in toluene, 306 g, 217 mmol) slowly at −15° C. After slurrying the resulting mixture for 1 h, the crude product from step 1 was added slowly. The reaction was then warmed up to RT and stirred for an additional hour. After cooling to 0° C., the reaction was quenched with 6% AcOH water solution (400 mL) and washed with a saturated aqueous $NaHCO_3$ solution. The organic layer was then treated with $MgCl_2$ (25 g, 263 mmol) and stirred for 3 h at RT. After filtration, the organic layer was treated with silica gel (100 g) and stirred for 30 min. After filtration, the solid was washed with toluene (2×100 mL). The filtrates were collected and concentrated in vacuum to give the crude product of Formula XIII in toluene, which was carried through the next step without further purification. $^1$H NMR (CDCl3, 400 MHz) δ 7.59, (1H, s), 7.38 (2H, s), 7.10-7.22 (10H, m), 6.15-6.22 (1H, dd), 5.50 (1H, s), 5.17 (1H, d), 5.02 (1H, d), 4.91 (2H, dd), 4.33 (1H, q), 3.65 (1H, broad), 3.48 (1H, broad),
1.26 (3H, d).

Step 3:

To the solution of the product of step 2 in toluene (300 mL), was added trimethylsilyl iodide (21 mL, 152.4 mmol) slowly. The resulting reaction mixture was stirred for 3 h. The reaction was then quenched with MeOH (12.4 mL, 305 mmol) and washed sequentially with 15% aq. $NaHSO_3$ (200 mL) followed by saturated aq. $NaHCO_3$ (200 mL). The organic layer containing the crude product of the free base of Formula XIII was carried through to the next stage without further purification.

Step 4:

To the above crude product of step 3 in toluene was added maleic acid (18 g, 155 mmol) dissolved in MeOH (50 mL). The resulting mixture was stirred for 1 h. The volume of the resulting solution was then reduced to 100 mL at 40° C. under vacuum distillation. At 40° C., n-heptane (100 mL) was added to the resulting solution. Upon cooling to RT, crystallization of the maleate salt occurred and additional n-heptane (500 mL) was added. After stirring 2 h, the solid was filtered and washed with toluene (400 mL), n-heptane (200 mL) and water (250 mL). The wet cake was dried at 45° C. under vacuum for 12 h to give the compound of Formula IVa (61 g; 77% yield from 619734-D). MP. 135° C.-140° C. $^1$H NMR (DMSO-$d_5$, 600 MHz) δ 8.87 (s, 2 H), 7.94 (s, 1H), 7.90 (s, 2H), 7.45 (t, 1H), 7.41 (t, 2H), 7.37 (d, 2H), 6.16 (dd, 1H), 6.06 (s, 2H), 5.47 (d, 1H), 5.36 (d, 1H), 4.83 (q, 1H), 3.97 (d, 1H), 3.83 (d, 1H), 1.43 (d, 3H). $^{13}$C NMR (DMSO-$d_s$, 500 MHz) ☐ 167.5, 146.6, 137.4, 136.4, 136.0, 130.8, 130.5, 130.3, 130.0, 128.5, 128.3, 126.9, 126.6, 126.1, 124.4, 122.3, 121.2, 120.1, 117.9, 76.6, 71.8, 62.1, 22.9. LC-MS exact mass calculated for [$C_{20}H_{20}F_6NO^+$] calculated: 404.14436. found: 404.14456.

EXAMPLE 2

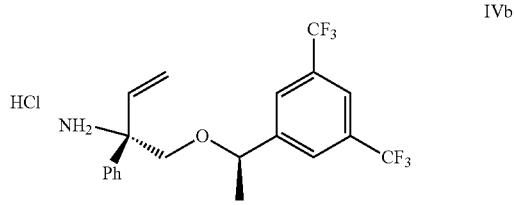 [SMILES: Cl ; C=C[C@@](N)(CO[C@H](C)c1cc(C(F)(F)F)cc(C(F)(F)F)c1)c1ccccc1]

[(1S)-1-({(1R)-1-[3,5-Bis(trifluoromethyl)phenyl]ethoxy}methyl)-1-phenylprop-2-enyl]amine, hydrochloride monohydrate To the solution of the crude product Step 3 from Example 1 (free base) in toluene was added conc. HCl (13 mL, 156 mmol, 37% in water). After stirring for 1 h, the volume of the resulting mixture was reduced to 200 mL at 40° C. under vacuum distillation and then water (6.6 mL, 465 mmol) was added. After cooling to RT, n-heptane (700 mL) was added slowly. The resulting slurry was stirred at RT for 6 h, then cooled to 0° C., and stirred for an additional 6 h. The product was filtered, washed with n-heptane (200 mL) and dried at RT under vacuum for 12 h to afford IVb as a white solid (51.8 g; 73% mol yield from XI). Mp. (with decomposition) 37° C. $^1$H NMR (CDCl₃, 400 MHz) δ 9.4 (bs, 3h), 7.8-7.4 (m, 8H), 6.2 (dd, 1H), 5.2 (m. 2h), 4.6 (q, 1H), 4.1 (d, 1h), 3.8 (s, 1H), 1.5 (d, 3h).

EXAMPLE 3

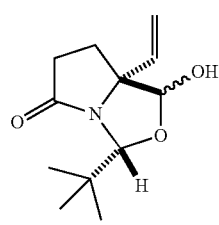

Step 1:

Preparation of (3R,6S)-3-tert-Butyldihydro-1H-pyrrolo[1,2-c][1,3]oxazole-1,5(6H)-dione

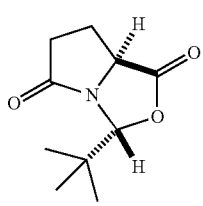

XIV

Method (a):

To a 250 mL three neck flask equipped with an agitator, thermometer, Dean Stark, reflux condenser, and a nitrogen inlet, were added L-pyroglutamic acid (20.0 g, 154.8 mmol), toluene (60 mL), diethylene glycol dimethyl ether (60 mL), trimethylacetaldehyde (40.0 g, 464.4 mmol), and CH₃SO₃H (1.5 g, 15.6 mmol). The reaction mixture was heated to reflux at 102-120° C. (reflux) for 14.5 h or until reaction completion with water removal via a Dean-Stark apparatus. The reaction mixture was cooled to 35° C. and distilled under vacuum to a final volume of 50 mL.

The mixture was cooled to 20° C. over 1 h, and n-heptane (140 mL) was added over 1h. The reaction mixture was cooled to −5° C. over 1 h and agitated for 1 h. The slurry was filtered and washed with heptane (60 mL) and water (60 mL), dried under vacuum at 50° C. to afford XIV (23.9 g, 79% yield) as an off-white crystalline solid. Mp (with decomposition) 116-168° C., ¹H-NMR (DMSO-d₆) δ 5.32 (s, 1H), 4.53 (t, J=8.1 Hz, 1H), 2.69 (m, 1H), 2.43 (m, 1H), 2.30 (m, 1H), 2.29 (m, 1H), 0.91 (s, 9H). LC/MS calculated for C₁₀H₁₆NO₃(M+H)⁺ (m/z): 197.231. found: 197.227.

Method (b):

To a 250 mL three neck flask equipped with an agitator, thermometer, reflux condenser, and a nitrogen inlet, was added L-pyroglutamic acid (200 g, 1.6 mol), NMP (400 mL), trimethylacetaldehyde (500 mL, 397 g, 4.6 mol), and CH₃SO₃H (30 mL 44.5 g, 0.46 mol). The reaction mixture was heated to 82.5° C. (reflux) for 15 min and TFAA (240 mL, 1.1 eq.) was added slowly over a period of 4.5 h. The temperature was maintained at 82.5° C. for an additional 4.5 h. The flask was cooled to 20° C. over 1 h and the mixture was transfer to a slurry of NaHCO₃ (325 g, 3.9 mmol) in water (2 L) at 5° C. over 1 h. The slurry was filtered and washed with ice-cold water (400 mL). The wet cake was then dried under vacuum at 50° C. to afford XIV (244 g, 72% yield) as an off-white crystalline solid.

Method (c):

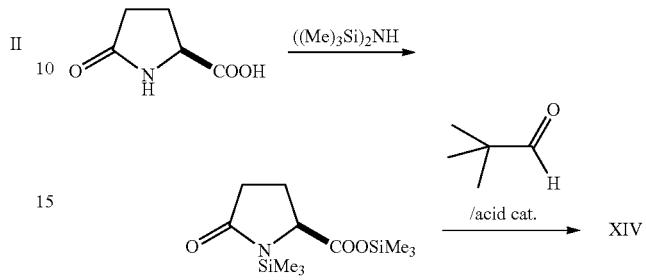

To a 250 mL three neck flask equipped with an agitator, thermometer, reflux condenser, and a nitrogen inlet, was added L-pyroglutamic acid (250 g, 1.94 mol), toluene (1000 mL), and (CH₃)₃SiNHSi(CH₃)₃ (890 mL, 4.26 mol). The mixture was heated to reflux for 6 h, during which time the reflux temperature slowly increased from 80 to 100° C. After 6 h, the mixture was distilled to a volume of 400 mL at 80 mm Hg and 50° C. Additional toluene (1000 mL) was charged and the mixture was distilled to a volume of 400 mL in vacuum. Then trimethylacetaldehyde (500 mL, 397 g, 4.6 mol), and CH₃SO₃H (30 mL 44.5 g, 0.46 mol) were charged and the reaction mixture was heated to 90° C. for 4 h. The reaction mixture was cooled to 35° C., toluene (1200 mL) was added and the mixture was distilled under vacuum to a final volume of 1000 mL. The flask was cooled to 20° C. and the mixture was transferred to a solution of NaHCO₃ (65 g) in water (1250 L) at −5° C. over 1 h. The slurry was filtered and washed with ice-cold water (400 mL) and then ice-cold isopropyl alcohol (100 mL). The wet cake was then dried under vacuum at 50° C. to afford the compound of Formula XIV (267 g, 68% yield) as an off-white crystalline solid.

Method (d):

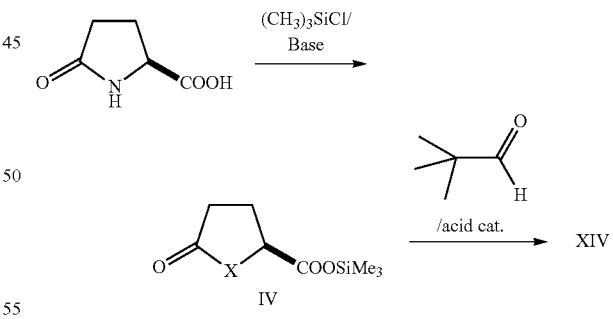

To a 1 L three neck flask equipped with an agitator, thermometer, reflux condenser and a nitrogen inlet, was charged L-pyroglutamic acid (50 g, 0.39 mol), toluene (450 mL) and Et₃N (113 mL 0.81 mol). (CH₃)₃SiCl (103 mL, 0.81 mol) was added while keeping the temperature below 30° C. The reaction mixture was heated to 110° C. and agitated for a period of 3 h. The suspension was cooled to 5° C. and diluted with heptane (100 mL). The triethylammonium hydrochloride salt was removed by filtration and washed with a toluene/heptane solution (200 mL). The filtrate was concentrated to a final volume of 150 mL and NMP (50 mL), trimethylacetaldehyde (100 mL, 0.78 mol) and CH$_3$SO$_3$H (2.5 mL, 0.04 mol) was added. The reaction mixture was heated to 80° C. for 24 h then cooled to 40° C. The reaction mixture was concentrated to about 100 mL and diluted with acetone (100 mL). The reaction mixture was transferred to a solution of NaHCO$_3$ (13 g) in water (250 mL) at 20° C. The suspension was cooled to 5° C. and stirred for 1 h. The slurry was filtered and washed with ice-cold water (50 mL) and then ice-cold isopropyl alcohol (50 mL). The product was then dried under vacuum at 45° C. to afford XIV (48.3 g, 63%) as an off-white crystalline solid.
Method (e):

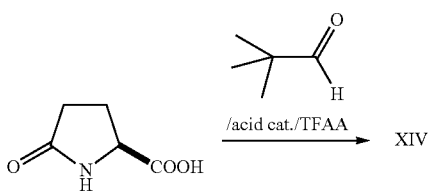

To a 1 L three neck flask equipped with an agitator, thermometer, reflux condenser and a nitrogen inlet, was charged L-pyroglutamic acid (20 g, 0.16 mol), trimethylacetaldehyde (50 mL, 0.39 mol), methane sulfonic acid (1.4 ml, 0.02 mol) toluene (140 mL) and N-methylpyrrolidone (20 mL). The mixture was heated to 90° C. and maintained at 90° C. whilst slowly adding trifluoroacetic anhydride (27 mL). The reaction was maintained at 90° C. for 8 hours, achieving 100% conversion of the acid.
Step 2:

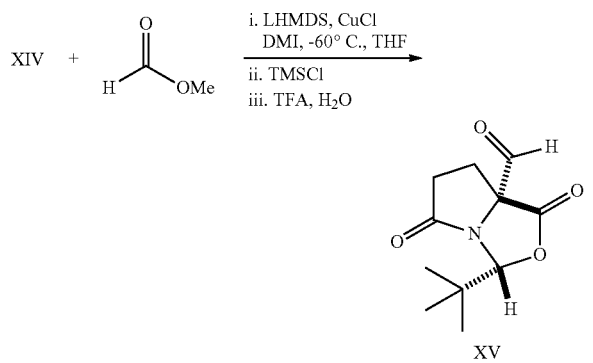

To a 2 L three neck flask equipped with an agitator, thermometer, reflux condenser, and a nitrogen inlet were charged XIV (100 g, 0.5 mol), CuCl (10 g), DMI (100 mL), THF (1.2 L), and methyl formate (100 mL). After cooling to below [−60]° C., LHMDS (700 mL, 1.0 M in THF) was charged at a rate such that the temperature did not exceed −60° C. After addition of LHMDS, TMSCl was charged at a rate such that the temperature did not exceed [−60]° C. The mixture was warmed to between 0 and 10° C. over 30 min and the batch was concentrated in vacuum to 250 mL and EtOAc (300 mL) was added. To a mixture of citric acid (120 g), water (1 L), and EtOAc (1 L) at 5° C. was then transferred the crude reaction mixture over 30 min while maintaining a temperature between 0 and 15° C. The flask containing the crude mixture was then rinsed with EtOAc (200 mL). After agitating for 10 min, the layers were separated and the organic layer was sequentially washed with 12.5% aq. citric acid (800 mL), 10% aq. citric acid (700 mL) and 8% aq. citric acid solution (600 mL). To a mixture of the organic layer and water (300 mL) at 5° C., was charged trifluoroacetic acid (30 mL) over 10 min while maintaining a temperature between 5 and 15° C. After completing the addition, the mixture was warmed to 25° C. and agitated for 3.5 h. An aqueous solution of KHCO$_3$ (200 mL, 20%) was charged over 30 min while maintaining a temperature below 20° C., followed by saturated NaCl solution (500 mL) and the layers were separated and split. The aqueous layer was back extracted with EtOAc (250 mL). The EtOAc fraction was washed with saturated NaCl solution (500 mL). Water (35 mL) was charged to the combined organic layers and the solution was concentrated in vacuum to a final volume of 100 mL. MTBE (400 mL) was charged and the mixture was concentrated in vacuum to a final volume of 100 mL. Additional MTBE (400 mL) was charged and the suspension was agitated for 2 h at RT. The resulting slurry was filtered, rinsed with MTBE (200 mL) and XV was obtained in 61% yield (70 g) after drying in vacuum at 45° C. for 12 h. MP 196° C.-198° C. $^1$H NMR (400 MHz in CDCl$_3$): δ 9.7 (s, 1 H), 5.5 (s, 1H), 2.7 (m, 1H), 2.6 (m, 1H), 2.4 (m, 2H), 0.9 (s, 9H). $^{13}$CNMR (400 MHz, CDCl$_3$): □ 192.0, 181.1, 169.7, 97.6, 73.4, 36.5, 31.7, 30.6, 24.6. ES-MS: [M+H$^+$]calcd for C$_{11}$H$_{15}$NO$_4$: 226.10. found: 226.27.
Step 3:

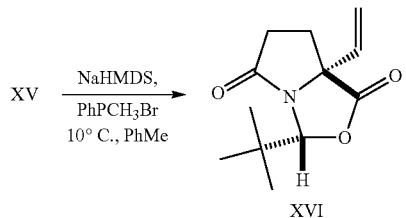

To a 3-neck 1-L flask equipped with a thermometer and mechanical stirrer were charged Ph$_3$PCH$_3$Br (122.9 g; 344.1 mmol) and toluene (100 mL). At 10° C., a solution of NaHMDS in toluene (540 mL, 13%) was added slowly to maintain the temperature at 10° C. This slurry was agitated at 10° C. for 1 h and then added slowly to a slurry of XV (50 g, 222 mmol) in toluene (100 mL) at 10° C., over a period of 2-4 h via peristaltic pump. After stirring for an additional hour, the batch was quenched into a solution of NaCl (10% aqueous), AcOH (38.5 mL, 666 mmol), and toluene (50 mL) over 30 min at 25° C. The resulting mixture was stirred for 30 min and the layers were settled, split and the lower aqueous layer was removed. The organic layer was then treated with MgCl$_2$ powder (70 g, 776 mmol) for 2 h at RT. The solids were then filtered off and the solid MgCl$_2$-triphenylphosphin oxide complex was washed with MTBE (100 mL). The organic filtrates were combined, washed with aq. NaCl (100 mL, 10%) and concentrated to 100 mL in vacuum. To the resulting slurry was charged heptane (400 mL) and the volume was reduced to 100 mL in vacuum. Additional heptane (400 mL) was added and the volume was reduced to 250 mL in vacuum. A third portion of heptane (400 mL) was added; the batch was then cooled to 0° C. over 2 h and stirred for another 2 h at this temperature. The solids were then removed by filtration and washed with ice-cold N-heptane (200 mL). The wet cake was dried under vacuum at 30° C. for 18 h to produce 62 g of XVI (63% yield) as an off-white solid. Mp 85° C.-87° C. $^1$H-NMR (CDCl$_3$) δ 5.98 (m, 1H), 5.31 (m, 3H), 2.56 (m, 1H), 2.17 (m, 3H), 0.81 (s, 9H). ES-MS: [M+H$^+$]calcd for C$_{12}$H$_{18}$NO$_3$: 224.12. found: 224.38.

Step 4:

To a 500 mL three-necked flask (1) equipped with an agitator, thermometer, and a nitrogen inlet were added XVI (30.0 g, 132 mmol) and THF (300 mL). After cooling mixture to −20° C., lithium tri(t-butoxy)aluminum hydride (1 M THF; 162 mL) was added over 2 h while maintaining the temperature around −20° C. Temperature was then raised to 0° C. over 12 h. The reaction is quenched with the addition of EtOAc (12.0 mL) over 30 min, followed by agitation for 30 min at 0° C., and then slow addition of glacial AcOH (12.0 mL) over 30 min. To another 1-L three-necked flask (2) equipped with an agitator, thermometer, and a nitrogen inlet were added finely ground sodium sulfate decahydrate (30 g, 93 mol) and THF (150 mL) at 0° C. The reaction mixture in flask (1) was slowly transferred to flask (2) containing the sodium sulfate decahydrate solution while maintaining the temperature at 0° C. The temperature of flask (2) was raised over a 1 h period and agitated for 1 h at 20° C. The contents of flask (2) were filtered, the wet cake was washed three times with THF (180 mL, 120 mL, and then 120 mL), and the filtrates were combined and concentrated in vacuum to 60 mL. To a 1000 mL three-necked flask (3) equipped with an agitator, thermometer, and a nitrogen inlet was added water (300 mL). The mixture from flask (2) was cooled to 5° C. and then added to the water with high agitation over a 2 h period, whereupon the product precipitated. The slurry was concentrated in vacuum to 450 mL and the solid was isolated via filtration. The wet cake was dried at 50° C. for 12 h to afford 25.1 g of the compound of formula H as a white/off white solid in 83% yield. Mp 88° C. $^1$H-NMR 500 MHz (DMSO-d$_6$) δ 6.92 (d, J=3.9 Hz, 1H), 6.03 (dd, J=15.8, 11.1 Hz, 1H), 5.36 (d, J=3.9 Hz, 1H), 5.24 (d, J=17.6 Hz, 1H), 5.11 (d, J=11.1 Hz, 1H), 4.75 (s, 1H), 2.72 (ddd, J=16.8, 10.2, 8.7 Hz, 1H), 2.28 (ddd, J=16.7, 10.5, 3.7 Hz, 1H), 2.45 (ddd, J=12.8, 10.4, 8.9 Hz, 1H), 1.82 (ddd, J=12.9, 10.5, 3.7 Hz, 1H), 0.85 (s, 9H). $^{13}$C-NMR (125 MHz DMSO-d$_6$) δ 180.7, 142.1, 113.3, 96.2, 93.9, 73.6, 34.5, 33.2, 26.8, 25.9 ppm. LC/MS calculated mass for C$_{12}$H$_{20}$NO$_3$ [M+H]+(m/z) 226.14377. found 226.14398.

EXAMPLE 4

5(R)-[[[I(S)-[[I(R)-[3,5-bis(trifluoromethyl)phenyl]ethoxy]methyl]-I-phenyl-2-propenyl]amino]methyl]-5-ethenyl-2-pyrrolidinone 4-methylbenzenesulfonate hydrate

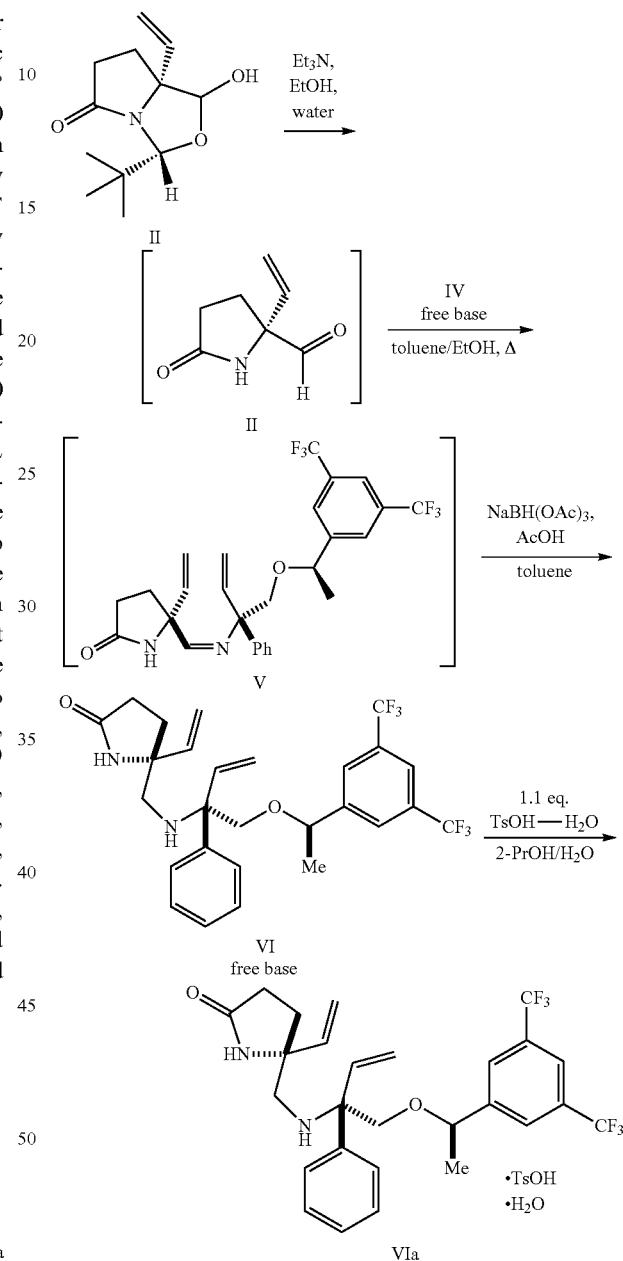

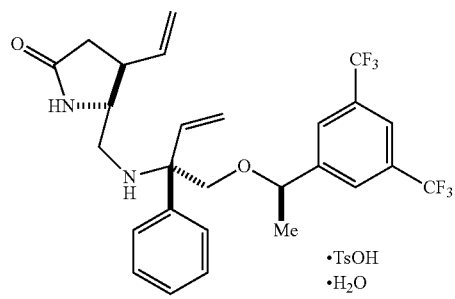

a) To a mixture of II (49.6 g, 0.22 mol) in EtOH (50 mL) and Et$_3$N (50 mL) was added water (50 mL) at RT. The resulting mixture was agitated at 25° C. After 4 h, more EtOH (350 mL) was added and the mixture was concentrated in vacuum to 180 mL.

b) To a mixture of IVa (100 g, 0.193 mol) in toluene (440 mL) was added at RT aq. NaOH (440 mL, 1 N). The reaction mixture was agitated at RT for 30 min. The aqueous layer was separated and the organic layer was washed twice with 10% NaCl aqueous solution (440 mL). The crude product IV freebase was used without further purification.

The crude solution of III in EtOH was then added to the above solution of IV free base in toluene and the resulting mixture was heated to reflux. Water was removed from reaction through azeotropic distillation and more toluene/EtOH (3/2 v/v) were added if necessary based on conversion. After reaction completion, EtOH was removed through solvent-exchange with toluene and the crude solution of V in toluene (530 mL) was slowly added to a mixture of NaBH(OAc)$_3$ (57.3 g, 0.27 mol) and AcOH (15.5 mL, 0.27 mol) in toluene (270 mL) at RT. The reaction mixture was agitated at RT for about 6 h, and then water (440 mL) was slowly added and the resulting mixture was agitated at RT for 1 h. The aqueous layer was separated and the organic layer was washed once with 5% NaHCO$_3$ aqueous solution (440 mL) and twice with 10% NaCl aqueous solution (440 mL) to obtain a solution of VI. Solvent was exchanged to isopropanol through vacuum distillation.

c) To the crude free base solution of VI in isopropanol (200 mL) was added at RT a solution of p-toluenesulfonic acid (40.4 g, 0.212 mol) in isopropanol (270 mL) followed by water (440 mL). The mixture was seeded with approximately 0.5 g of crystalline VIa and agitated at RT for 1 h before addition of more water (880 mL). After agitation for 8 h at RT, the crystals were collected by filtration, washed with isopropanol/water, water and heptanes, and dried to give VIa as a white crystalline powder (122 g, yield 88% based on V). Mp 80.2-93.4° C. $^1$H NMR (CDCl$_3$, 400 MHz) δ 9.52 (bs, 1H), 8.80 (bs, 1H), 8.33 (s, 1H), 7.74 (d, J=8.1 Hz, 2H), 7.73 (s, 1H), 7.55 (s, 2H), 7.52-7.50 (m, 2H), 7.37-7.29 (m, 3H), 7.16 (d, J=8.0 Hz, 2H), 6.22 (dd, J=17.5, 11.1 Hz, 1H), 5.90 (dd, J=17.2, 10.6 Hz, 1H), 5.56 (d, J=11.0 Hz, 1H), 5.34 (d, J=17.1 Hz, 1H), 5.25 (d, J=17.5 Hz, 1H), 5.23 (d, J=10.6 Hz, 1H), 4.79 (q, J=6.3 Hz, 1H), 4.35 (d, J=10.5 Hz, 1H), 3.83 (d, J=10.4 Hz, 1H), 3.35-3.18 (m, 2H), 2.35 (s, 3H), 2.35-2.15 (m, 3H), 2.00-1.91 (m, 1H), 1.39 (d, J=6.4 Hz, 3H).

EXAMPLE 5

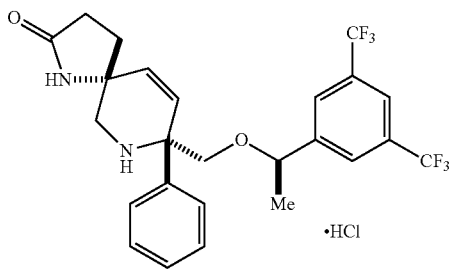

VIIa (5R,8S)-8-[1-(R)-(3,5-Bis-trifluoromethyl-phenyl)-ethoxymethyl]-8-phenyl-1,7-diaza-spiro[4.5]dec-9-en-2-one, hydrochloride A solution of 130.0 g (181.4 mmol) of VIa (VI p-toluenesulfonic acid (TsOH) monohydrate) and 51.7 g (272.1 mmol) of toluenesulfonic acid in toluene (3.25 L) was distilled under reduced pressure (60-80 mm Hg) at 50° C. to a final volume of 1.95 L. Upon completion of the distillation, the toluene solution containing VIa and toluenesulfonic acid was evacuated to ~80 mm Hg and then purged with N$_2$ via a submersed needle. This sparging process was repeated two times. In a second reactor, 1.14 g (1.8 mmol) of Hoveyda-Grubbs' Second Generation Catalyst (HG-II), having the structure

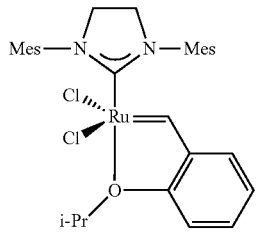

was dissolved in anhydrous, degassed toluene (650 mL, prepared in a manner identical to the above toluene solution). This catalyst solution was slowly charged to the first reactor over 30 min at between 60 to 80° C. The reaction mixture was stirred at the same temperature range for 4 h and the conversion is monitored by HPLC. Upon completion of the reaction, a 16% solution of aq. Na$_2$S$_2$O$_5$ (650 mL) was added to the reactor over 30 min and stirred at 60 to 80° C. for 3 h, after which the mixture was cooled to 25° C. and an aq. 0.5 N NaHCO$_3$ solution was added (650 mL). The biphasic mixture was then stirred at 25° C. for 1 h, allowed to settle and the lower aqueous layers and interface were removed. The organic phase was washed with 0.5 N aq. NaHCO$_3$ (1.3 L), then 10% aq. NaCl (1.3 L) and finally water (1.3 L). The organic phase was filtered through a pad of celite and to the filtrate was charged 12 N aq. HCl (14.4 mL). The toluene/H$_2$O was concentrated to below 390 mL under vacuum (50-60 mm Hg) at a temperature above 50° C. The resulting solution was cooled to 45° C. and seeded with VIIa in heptanes (65 mL). After 30 min of stirring at 45° C., the reaction mixture was cooled from 45° C. to 20° C. over 6 h. Then heptanes (1.82 L) were charged to the reaction mixture at 20° C. over 3 h. The solid precipitate was filtered and washed with heptanes (520 mL). The wet cake was dried at 25° C. for 4 h then 65° C. in a vacuum oven overnight to afford 83 g of VIIa (85% yield) as a grayish-to of-white colored solid. In addition, the aqueous layers can be combined and filtered to recover the Ru-salts. Mp 190-195° C. $^1$H NMR (400 MHz, CDCl$_3$) δ 10.58 (bs, 1H), 10.21 (bs, 1H), 8.25 (s, 1H), 7.70 (s, 1H), 7.58-7.43 (m, 7H), 6.16 (d, J=11, 1H), 6.05 (d, J=11, 1H), 4.65 (q, J=6 Hz, 1H), 4.23 (d, J=9.4 Hz, 1H), 3.81 (d, J=13.6 Hz, 1H), 3.73 (d, J=9.5 Hz, 1H), 2.99 (app. t, J=11 Hz, 1H), 2.48-2.40 (m, 2H), 2.06-1.94 (m, 2H), 1.43 (d, J=6.4 Hz, 1H); $^{13}$C NMR (100.6 MHz, CDCl$_3$) δ 176.7, 145.8, 135.1, 132.5, 132.4, 132.0, 130.0, 129.7, 127.5, 127.0, 126.5, 124.8, 122.1, 122.0, 122.0, 78.4, 73.1, 63.5, 55.9, 50.0, 32.2, 29.6, 24.3 ppm. ES-MS: [M+H$^+$] calcd for C$_{25}$H$_{25}$F$_6$N$_2$O$_2$: 499.18. found: 499.05.

EXAMPLE 5a

Reduction of Metathesis Catalyst in the Presence of a PTC

Example 5 was repeated as described above until HPLC indicated complete conversion of the compound of Formula VIa to the compound of Formula VIIIa. Upon completion of the reaction, a 16% solution of aq. Na$_2$S$_2$O$_5$ (650 mL) was added to the reactor over 30 min along with 2.5 g of tetra-n-butyl-ammonium chloride. The mixture was stirred for 0.7 hours maintaining the reaction mixture at a temperature between 60° C. and 80° C., after which the mixture was cooled to 25° C. and an aq. 0.5 N NaHCO$_3$ solution was added (650 mL). The biphasic mixture was then stirred at 25° C. for 1 h, allowed to settle and the lower aqueous layers and interface were removed, and the reaction mixture worked up as described in Example 5. The results were the same, demonstrating the advantage provided by the use of a PTC in reducing the metathesis catalyst via the process of Scheme 4 described herein above.

EXAMPLE 6

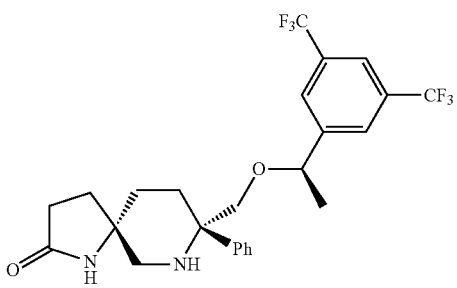

VIII (5S,8S)-8-[1-(R)-(3,5-Bis-trifluoromethyl-phenyl)-ethoxymethyl]-8-phenyl-1,7-diaza-spiro[4.5]decan-2-one hydrochloride hydrate To a mixture of VIIa (100 g, 0.187 mol) in toluene (600 mL) was charged aqueous NaOH (5%, 300 mL). After agitating the mixture for 15 min, the organic layer was separated and washed with brine (10%, 2×500 mL). The organic layer was then subjected to hydrogenation with Pd/C (10 g, 10% in carbon 50% wet) and Nuchar-Aquaquard (50 g) under 60 to 80 psi pressure for 4 to 8 h or until reaction completion. The reaction was filtered through a pad of celite. The celite was washed with toluene (100 mL). The combined toluene solution was concentrated to 500 mL. A solution of aqueous HCl (~35%, 20 ml, ~1.3 eq) was slowly added into the reaction solution and the mixture was slowly cooled down to 0° C. The product was collected by filtration and washed with a solution of toluene and MTBE (1:1). The wet cake was dried at 40 to 45° C. to give 95 g of VIII (95% yield) as a white to off-white solid. Mp152-154° C.

$^1$H NMR (400 MHz in DMSO-d$_6$): δ 10.62 (dd, J=10, 12 Hz, 1H, N—H), 9.62 (d, J=12 Hz, 1H, N—H), 7.92 (br, NH), 7.92 (s, 2H), 7.66 (s, 1H), 7.58 (d, J=7.5 Hz, 2H), 7.44 (m, 2H), 7.40 (m, 1H), 4.65 (q, J=6.4 Hz, 1H), 4.30 (d, J=10 Hz, 1H), 3.36 (d, J=10 Hz, 1H), 3.22 (d, J=13 Hz, 1H), 2.88 (dd, J=13, 10 Hz, 1H), 2.49 (md, J=14.5 Hz, 1H), 2.19 (md, J=14.5 Hz, 1H), 2.15 (m, 1H), 2.24 (m, 1H), 1.88 (m, 1H), 1.67 (m, 1H), 1.41 (d, J=6.4 Hz, 3H), 1.79 (md, J=13.5 Hz, 1H), 1.39 (md, J=13.5 Hz, 1H); $^{13}$C NMR (100 MHz, DMSO): δ 175.3, 146.6, 134.7, 130.1 (2) ($^2$J$_{CF}$=33 Hz), 128.5 (2), 128.0, 126.4 (2), 126.3 (2) ($^3$J$_{CF}$=2.6 Hz), 120.9 ($^3$J$_{CF}$=3.7 Hz), 119.9 (2) (J$_{CF}$=273 Hz), 75.8, 73.2, 63.1, 55.6, 48.9, 31.2, 30.8, 28.8, 24.8, 23.1.

EXAMPLE 7

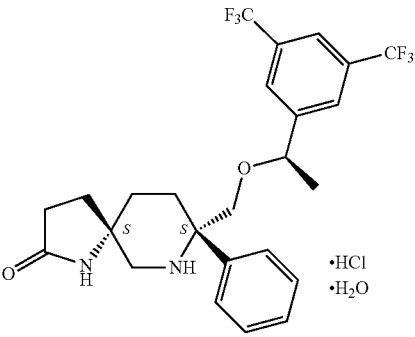

Ia (5S,8S)-8-(1-(R)-[3,5-Bis(trifluoromethyl)phenyl]ethoxy)methyl)-8-phenyl-1,7-diazaspiro[4.5]decan-2-one hydrochloride monohydrate Method 1: VIII (20 g) was suspended in 155.0 g of an EtOH-isopropanol-water-HCl stock solution (stock solution preparation: 168.6 g absolute EtOH, 368.7 g water, 11.6 g of isopropanol, 1.6 g of 37% HCl) and heated to reflux (78-79° C.) until a clear solution was obtained. The mixture was then cooled slowly to a temperature between 72 and 73° C. and optionally, seeded with 0.4 g of micronized Ia suspended in 20 ml of the stock solution. The amount of seed used can be varied between 0.0 and 2.0 g to effect changes in the particle size distribution (PSD) of the product. The batch was further cooled to 0° C. at a rate of 0.5° C./min, filtered under vacuum and washed with 40 mL of stock solution. Finally, the batch was dried under vacuum at a temperature of 40° C. for at least 18 h to give 18.7 g (91.2%) of Ia as white solid.

Method 2: Thirty grams of VIII was suspended in 231-232 g of a 40:60% by volume EtOH-water stock solution (stock solution preparation: 400 mL EtOH (95% EtOH, 5% MeOH), 600 mL water) and heated to reflux (78-79° C.) until a clear solution was obtained. The mixture was then cooled slowly to a temperature between 67.5 and 68.5° C. and seeded with 1.5 g of micronized Ia suspended in 30 mL of the stock solution. The amount of seed used can be varied between 0.0 and 3.0 g to effect changes in the PSD of the product. The batch was further cooled to 0° C. at a rate of 0.5° C./min and an additional 35 g of water was added to improve yield. The batch was filtered under vacuum and washed with 60 mL of a 35:65 by volume EtOH:water solution. Finally, the batch was dried under vacuum at a temperature of 40° C. for at least 18 h to produce 28.2-28.9 g (89.6-91.8%) of 1a.

Method 3: VIII (11.6 g) was dissolved at RT in EtOH (47 mL). To the solution, water (186 mL) was added over about 35 min and the temperature of the suspension was maintained at 25° C. The resulting suspension was cooled to 0° C. to improve yield and agitated for 30 min. The batch was then filtered under vacuum and washed with 25 mL of a 20:80 by volume EtOH:water solution. Finally, the batch was dried under vacuum at a temperature of 40° C. for at least 18 h. Yield: 9.7 g (83.6%).

Method 4: VIII (22.9 g) was dissolved at RT in EtOH (76 mL). The solution was then filtered and added over about 25 min to water (366.8 g). The resulting suspension was cooled to 0° C. to improve yield and agitated for 30 min. The batch was then filtered under vacuum and washed with 70 mL of a 20:80 by volume EtOH:water solution. Finally, the batch was dried under vacuum at a temperature of 40° C. for at least 18 h. Yield: 20.4 g (89.1%).

Method 5: VIII (16.4 g) was suspended at 25° C. in toluene (115 mL). 50 mL of a 1N NaOH solution was added to the suspension and the batch was agitated for 30-60 min. The batch was then allowed to split for about 30 min and the aqueous bottom layer was removed. To the organic layer, 2.82 g of 37% HCl was added to form and precipitate Ia, the monohydrate hydrochloride salt. The batch was stirred for 30 min and then filtered under vacuum and washed with toluene (32 mL). Finally, the batch was dried under vacuum at a temperature of 40° C. for at least 18 h to afford 12.4 g (75.6%) of Ia.

Using similar procedures, isomers Ib to Ih were prepared. The physical data for the compounds is as follows:

Formula Ib (S,R,R):

Isolated as a pale brown oil after column chromatography. $^1$H NMR (400 MHz in DMSO-$d_6$): δ 10.23 (dd, J=10, 12 Hz, 1 H, N—H), 9.68 (d, J=12 Hz, 1H, N—H), 7.93 (s, 1H), 7.75 (s, 2H), 7.61 (d, J=7.5 Hz, 2H), 7.42 (m, 2H), 7.35 (m, 1H), 4.53 (q, J=6.4 Hz, 1H), 3.82 (d, J=10 Hz, 1H), 3.67 (d, J=10 Hz, 1H), 3.00 (d, J=13 Hz, 1H), 2.65 (dd, J=13, 10 Hz, 1H), 2.46 (md, 2H), 2.15 (m, 1H), 2.24 (m, 1H), 1.81 (m, 1H), 1.14 (d, J=6.4 Hz, 3H), 1.53 (md, J=13.5 Hz, 1H), 1.62 (md, J=13.5 Hz, 1H); $^{13}$C NMR (100 Mhz, DMSO): δ 175.9, 147.1, 134.9, 130.4 (2) ($^2J_{CF}$=33 Hz), 130.0 (2), 128.5, 127.0 (2), 125.0 (2) ($^3J_{CF}$=2.6 Hz), 122.3 ($^3J_{CF}$=3.7 Hz), 121.3 (2) ($J_{CF}$=273 Hz), 76.5, 73.7, 62.9, 56.0, 47.5, 31.1, 30.9, 29.4, 25.6, 22.8. MS. Calculated for $C_{25}H_{26}F_6N_2O_2.HCl.H_2O$, (M+H)$^+$500.47 (m/z): 500.19.

Formula Ic (R,S,R):

Isolated as an off-white solid from diethyl ether. $^1$H NMR (400 MHz in DMSO-$d_6$): δ 7.95 (d, J=12 Hz, 1H, N—H), 7.79 (d, J=7.5 Hz, 2H), 7.52 (md, 2H), 7.43 (d, J=7.5 Hz, 1H), 7.32 (m, 2H), 7.21 (m, 1H), 4.55 (q, J=6.4 Hz, 1H), 3.28 (d, J=10 Hz, 1H), 3.11 (d, J=10 Hz, 1H), 2.50 (d, J=13 Hz, 1H), 2.40 (d, J=13, 1H), 2.22 (md, 2H), 2.18 (m, 2H), 1.76 (m, 2H), 1.30 (d, J=6.4 Hz, 3H), 1.45 (md, J=13.5 Hz, 2H); $^{13}$C NMR (100 Mhz, DMSO): δ 175.9, 147.9, 142.2, 130.6 (2) ($^2J_{CF}$=33 Hz), 129.8 (2), 128.4, 127.5 (2), 126.6 (2) ($^3J_{CF}$=2.6 Hz), 125.0, 122.3, 121.2 (2), 78.4, 76.4, 58.4, 57.4, 50.4, 33.3, 29.8, 27.9, 23.6. MS. Calculated for $C_{25}H_{26}F_6N_2O_2.HCl.H_2O$, (M+H)$^+$ 500.47 (m/z): 500.18.

Formula Id (R,R,R):

Isolated after purification by column chromatography, via trituration in 1:2 diethyl ether/heptane as an off white solid. $^1$H NMR (400 MHz in DMSO-$d_6$): δ 9.71 (dd, J=10, 12 Hz, 1H, N—H), 8.92 (d, J=12 Hz, 1H, N—H), 8.51 (br, NH), 7.99 (s, 1H), 7.88 (s, 2H), 7.66 (d, J=7.5 Hz, 2H), 7.52 (m, 2H), 7.48 (m, 1H), 4.61 (q, J=6.4 Hz, 1H), 4.03 (d, J=10 Hz, 1H), 3.78 (d, J=10 Hz, 1H), 3.22 (d, J=13 Hz, 1H), 2.88 (m, J=13, 10 Hz, 1H), 2.49 (md, J=14.5 Hz, 1H), 2.19 (md, J=14.5 Hz, 1H), 2.25 (m, 3H), 1.90 (m, 2H), 1.87 (md, 1H), 1.72 (md, J=13.5 Hz, 1H), 1.28 (d, J=6.5 Hz, 3H); $^{13}$C NMR (100 Mhz, DMSO-$d_6$): δ 173.6, 147.0, 135.4, 130.2 (2) ($^2J_{CF}$=33 Hz), 129.0, 128.6, 127.8 (2), 127.0, 126.3 (2) ($^3J_{CF}$=2.6 Hz), 120.9, 122.3, 121.4, 119.6, 76.6, 73.3, 63.4, 52.9, 49.1, 31.5, 29.2, 24.9, 22.6. MS. Calculated for $C_{25}H_{26}F_6N_2O_2.HCl.H_2O$, (M+H)$^+$500.47 (m/z): 500.34

Formula Ie (S,S,S)

Isolated as a fine white HCl salt by triturating in diethyl ether at 10° C. for 3 hours after column chromatography. $^1$H NMR (400 MHz in DMSO-$d_6$): δ 10.58 (dd, J=10, 12 Hz, 1H, N—H), 76 (d, J=12 Hz, 1H, N—H), 8.57 (s, 1H), 8.11 (s, 1H), 7.89 (d, J=12 Hz, 2H), 7.61 (d, J=10 Hz, 2H), 7.55 (m, 3H), 4.66 (q, J=6.4 Hz, 1H), 4.09 (d, J=10 Hz, 1H), 3.83 (d, J=10 Hz, 1H), 3.27 (d, J=13 Hz, 1H), 2.65 (dd, J=13, 10 Hz, 1H), 2.35 (md, 2H), 2.29 (m, 1H), 1.97 (m, 1H), 1.32 (d, J=6.4 Hz, 3H), 1.58 (dd, J=13.5 Hz, 9 Hz, 1H), 1.78 (md, J=13.5 Hz, 1H); $^{13}$C NMR (100 MHz, DMSO-$d_6$): δ 175.7, 147.0, 134.9, 130.4 (2) ($^2J_{CF}$=33 Hz), 130.0 (2), 128.5, 127.0 (2), 126.9 (2) ($^3J_{CF}$=2.6 Hz), 122.3 ($^3J_{CF}$=3.7 Hz), 121.4 (2) ($J_{CF}$=273 Hz), 76.6, 73.7, 63.1, 56.0, 47.8, 31.6, 31.1, 29.2, 25.9, 22.9. MS. Calculated for $C_{26}H_{26}F_6N_2O_2.HCl.H_2O$, (M+H)$^+$500.47 (m/z): 500.4

Formula If (S,R,S):

After purification by column chromatography, isolated as an off-white HCl salt from diethyl ether. $^1$H NMR (400 MHz in DMSO-$d_6$): δ 10.30 (dd, J=10, 12 Hz, 1H, N—H), 9.81 (d, J=12 Hz, 1H, N—H), 8.11 (s, 1H), 7.86 (s, 1H), 7.58 (m, 4H), 7.46 (m, 4H), 4.84 (q, J=6.4 Hz, 1H), 4.28 (d, J=13 Hz, 1H), 3.59 (s, 1H), 3.52 (d, J=10 Hz, 1H), 3.36 (d, J=10 Hz, 1H), 3.01 (d, J=13 Hz, 1H), 2.72 (dd, J=13, 10 Hz, 1H), 2.43 (md, 2H), 2.08 (m, 2H), 1.57 (d, J=6.4 Hz, 3H), 1.85 (md, J=13.5 Hz, 1H), 1.72 (md, J=13.5 Hz, 1H); $^{13}$C NMR (100 Mhz, DMSO-$d_6$): δ 175.7, 147.1, 134.6, 130.7 (2) ($^2J_{CF}$=33 Hz), 130.3 (2), 128.9, 128.4 (2), 126.8 (2) ($^3J_{CF}$=2.6 Hz), 122.3 ($^3J_{CF}$=3.7 Hz), 121.3 (2) ($J_{CF}$=273 Hz), 76.2, 73.7, 66.9, 49.3, 43.8, 31.1, 31.6, 29.2, 25.2, 23.5. MS. Calculated for $C_{25}H_{26}F_6N_2O_2.HCl.H_2O$, (M+H)$^+$500.47 (m/z): 500.3

Formula Ig (R,S,S)

Isolated as an off-white HCl salt triturated in diethyl ether at 5° C. for 12 hours after purification by column chromatography. $^1$H NMR (400 MHz in DMSO-$d_6$): δ 10.00 (dd, J=10, 12 Hz, 1H, N—H), 9.64 (d, J=12 Hz, 1H, N—H), 7.94 (s, 1H), 7.78 (s, 2H), 7.63 (d, J=7.5 Hz, 2H), 7.41 (m, 2H), 7.37 (m, 1H), 4.55 (q, J=6.4 Hz, 1H), 3.82 (d, J=10 Hz, 1H), 3.69 (d, J=10 Hz, 1H), 3.10 (d, J=13 Hz, 1H), 2.76 (dd, J=13, 10 Hz, 1H), 2.20 (md, 2H), 2.15 (m, 1H), 1.94 (m, 1H), 1.83 (m, 1H), 1.14 (d, J=6.4 Hz, 3H), 2.44 (md, J=13.5 Hz, 2H); $^{13}$C NMR (100 Mhz, DMSO-$d_6$): δ 175.8, 147.1, 134.9, 130.2 (2) ($^2J_{CF}$=33 Hz), 129.0 (2), 127.8, 127.0 (2), 125.0 (2) ($^3J_{CF}$=2.6 Hz), 122.3 ($^3J_{CF}$=3.7 Hz), 121.3 (2) ($J_{CF}$=273 Hz), 76.5, 73.7, 62.9, 56.0, 47.5, 31.1, 30.9, 29.4, 25.7, 22.8. MS. Calculated for $C_{25}H_{26}F_6N_2O_2.HCl.H_2O$, (M+H)$^+$500.47 (m/z): 500.33

Formula Ih (R,R,S):

Isolated as the HCl salt by trituration in diethyl ether at 5° C. for 3 hours after purification by column chromatography. $^1$H NMR (400 MHz in DMSO-$d_6$): δ 9.56 (dd, J=10, 12 Hz, 1H, N—H), 9.42 (d, J=12 Hz, 1H, N—H), 7.97 (s, 1H), 7.97 (s, 1H), 7.52 (s, 2H), 7.46 (d, J=7.5 Hz, 2H), 7.41 (m, 2H), 7.35 (m, 1H), 4.60 (q, J=6.4 Hz, 1H), 4.20 (d, J=10 Hz, 1H), 3.59 (s, J=10 Hz, 1H), 3.16 (d, J=13 Hz, 1H), 2.87 (dd, J=13, 10 Hz, 1H), 2.19 (md, 2H), 2.12 (m, 1H), 1.94 (m, 1H), 1.72 (m, 1H), 1.36 (d, J=6.4 Hz, 3H), 1.63 (md, J=13.5 Hz, 1H), $^{13}$C NMR (100 Mhz, DMSO-$d_6$): δ 175.8, 147.1, 131.2, 130.4 ($^2$) ($^2J_{CF}$=33 Hz), 130.1 (2), 128.5, 126.7 (2), 124.9 (2) ($^3J_{CF}$=2.6 Hz), 122.2 ($^3J_{CF}$=3.7 Hz), 121.3 (2) ($J_{CF}$=273 Hz), 119.5, 76.3, 73.7, 66.1, 56.1, 47.6, 31.1, 30.9, 26.1, 23.8. MS. Calculated for $C_{25}H_{26}F_6N_2O_2.HCl.H_2O$, (M+H)$^+$ 500.47 (m/z): 500.3

The above description of the invention is intended to be illustrative and not limiting. Various changes or modifications in the embodiments described herein may occur to those skilled in the art. These changes can be made without departing from the scope or spirit of the invention

What is claimed is:
1. A compound of the following formulae:
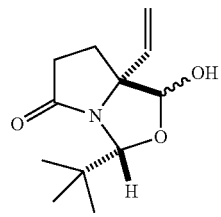
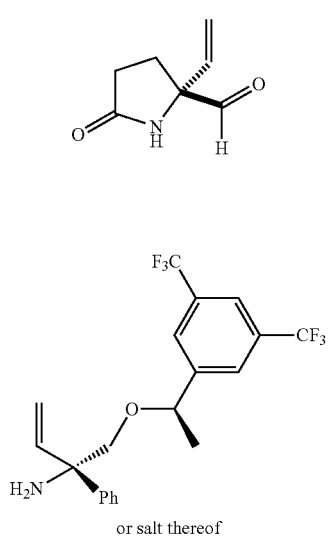
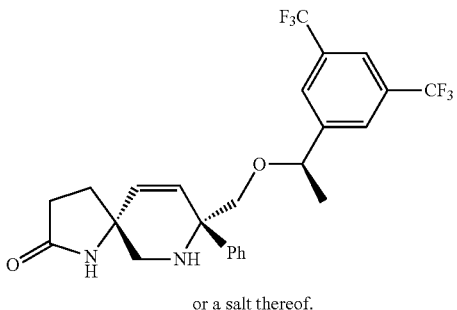
or a salt thereof.
2. The compound of claim 1, having a structure according to the following formula,
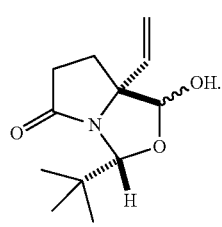
3. The compound of claim 1, having a structure according to the following formula,
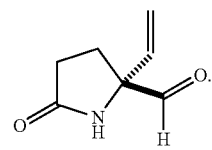
4. The compound of claim 1, having a structure according to the following formula,
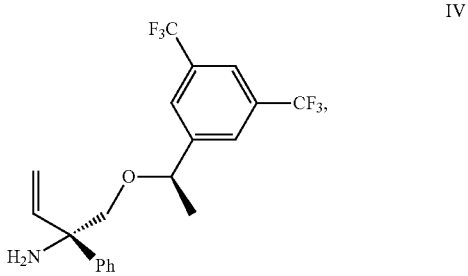 [SMILES: C=C[C@@](N)(CO[C@H](C)c1cc(C(F)(F)F)cc(C(F)(F)F)c1)c1ccccc1]
or a salt thereof.

5. The compound of claim 1, having a structure according to the following formula,
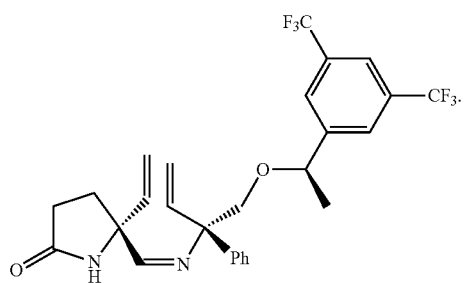
V
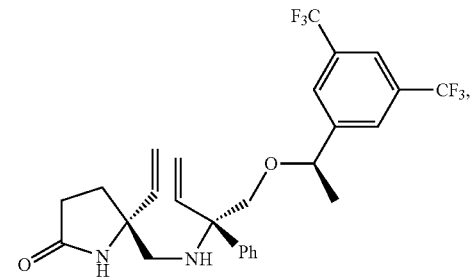
VI
or a salt thereof.
7. The compound of claim 1, having a structure according to the following formula,
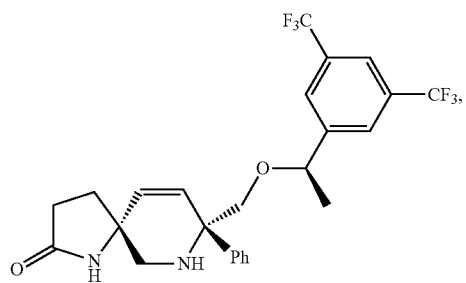
VII
6. The compound of claim 1, having a structure according to the following formula,
or a salt thereof.
* * * * *